US012653915B2

(12) United States Patent
Dencovski et al.

(10) Patent No.: US 12,653,915 B2
(45) Date of Patent: Jun. 16, 2026

(54) SYSTEM FOR DISINFECTION OF SURFACES AND/OR ROOM AIR

(71) Applicant: Siemens Healthcare GmbH, Erlangen (DE)

(72) Inventors: Kristian Dencovski, Erlangen (DE); Mario Bechtold, Hemhofen (DE); Franz Dirauf, Bad Staffelstein (DE)

(73) Assignee: Siemens Healthineers AG, Erlangen (DE)

( * ) Notice: Subject to any disclaimer, the term of this patent is extended or adjusted under 35 U.S.C. 154(b) by 1189 days.

(21) Appl. No.: 17/555,818

(22) Filed: Dec. 20, 2021

(65) Prior Publication Data

US 2022/0193281 A1 Jun. 23, 2022

(30) Foreign Application Priority Data

Dec. 21, 2020 (DE) .......................... 102020216423.1

(51) Int. Cl.
| | |
|---|---|
| *A61L 2/10* | (2026.01) |
| *A61L 2/24* | (2006.01) |
| *F24F 8/22* | (2021.01) |
| *A61L 103/15* | (2026.01) |

(52) U.S. Cl.
CPC .................................... *A61L 2/10* (2013.01); *A61L 2/24* (2013.01); *F24F 8/22* (2021.01); *A61L 2103/15* (2026.01); *A61L 2202/11* (2013.01); *A61L 2202/14* (2013.01); *A61L 2202/15* (2013.01); *A61L 2202/16* (2013.01)

(58) Field of Classification Search
CPC ........................................................ A61L 2/10
See application file for complete search history.

(56) References Cited

U.S. PATENT DOCUMENTS

| | | | | |
|---|---|---|---|---|
| 9,345,799 | B1 * | 5/2016 | Wind | ..................... B43K 23/02 |
| 2012/0126134 | A1 | 5/2012 | Deal et al. | |
| 2016/0074546 | A1 * | 3/2016 | Rizzone | ................... A61L 2/10 |
| | | | | 250/455.11 |
| 2017/0296686 | A1 * | 10/2017 | Cole | ........................ A61L 2/26 |

(Continued)

FOREIGN PATENT DOCUMENTS

| | | |
|---|---|---|
| DE | 102011109083 A1 | 2/2013 |
| DE | 202017100914 U1 | 4/2017 |

OTHER PUBLICATIONS

Weisstechnik—mediclean: Clean air systems in operating theatres—https://www.weiss-technik.com/fileadmin/Redakteur/Mediathek/Broschueren/WeissTechnik/Klimatechnik/Weiss-Technik-MS-OP-Decken-EN.pdf (Stand: Nov. 29, 2021).

(Continued)

*Primary Examiner* — Donald R Spamer
(74) *Attorney, Agent, or Firm* — Banner & Witcoff, Ltd.

(57) ABSTRACT

The present disclosure is directed to system and a method for disinfection of surfaces and/or room air, wherein at least one UV source is arranged on a medical device and/or in a medical examination and/or treatment room in such a way that it is suitable for disinfection irradiation of at least one surface and/or at least one flow of air. Advantageously, the at least one UV source is attached to a component able to be moved mechanically for the purpose of medical examination or treatment. The disclosure also relates to a control method for the system, which includes the automatic execution of hygiene programs.

16 Claims, 14 Drawing Sheets

(56) References Cited

U.S. PATENT DOCUMENTS

2018/0188340 A1 * 7/2018 Garcia ................. H02K 13/006
2018/0339073 A1 * 11/2018 Clynne ................. A61L 2/0047

OTHER PUBLICATIONS

Dai T. et al: Ultraviolet C-irradiation: an alternative antimicrobial approach to localized infections? Expert Rev Anti Infect Ther.*2012, 10 185-95*(PMC free article)(PubMed)(Google Scholar).
Normeditec Nordic Medicine Technology—Laminar Air Flow Blanket Tripod, https://www.operio.eu/Deckenstativ.aspx, Nov. 29, 2021.
Normeditec Nordic Medicine Technology—SteriStay instrument table with integrated TAV flow: with the sterile Instruments enrichment table, the instruments and implants are protected from re-contamination with bacteria even during very long operations—Nov. 29, 2021, https://www.operio.eu/Instrumententisch.aspx.
Normeditec Nordic Medicine Technology—Mobile laminar air flow device for operating theatres—Nov. 29, 2021, https://www.operio.eu/OperioMobil.aspx.
Normeditec Nordic Medicine Technology—Field hospital operating room—hospital for corona patients: Operio sterile air flow with Hepa H 14 filter system eliminates over 99.9% of coronaviruses—can be used immediately, Nov. 29, 2021 https://www.operio.eu/FeldOP.aspx.
Luftreinigerdepot your specialist for healthy indoor air since 2016(Ihr Spezialist fur gesunde Raumluft seit 2016), IQAir breath air purifier—https://www.luftreinigerdepot.de/iqair-luftreiniger-atem—English version as of Nov. 29, 2021.
Germitec—UV-C High Level Disinfection (HLD) https://www-germitec.com/en/antigermix/—Jul. 24, 2020.
Luftreinigerdepot your specialist for healthy indoor air since 2016(Ihr Spezialist fur gesunde Raumluft seit 2016)—Blueair Pro XL air purifier—https://www.luftreinigerdepot.de/blueair-pro-xl-luftreiniger—English version as of Nov. 29, 2021.
Disinfection Robot Yezhik UVD, Medical Robots—UV Disinfection and Remote Assistance, Aitheon, https://aitheon.com/medical-robots, pp. 1-12, Jul. 24, 2020.

* cited by examiner

SYSTEM FOR DISINFECTION OF SURFACES AND/OR ROOM AIR

CROSS-REFERENCE TO RELATED APPLICATIONS

The present application claims the benefit of the filing date of Germany patent application no. DE 10 2020 216 423.1, filed on Dec. 21, 2020, the contents of which are incorporated herein by reference in their entirety.

TECHNICAL FIELD

The disclosure relates to a system and method for disinfection of surfaces and/or room air and to a method for controlling such a system.

BACKGROUND

The process of operating medical devices may result in a contamination of the devices, in particular of the operating surfaces, handles or support surfaces with pathogens (inter alia bacteria, viruses, germs). Likewise, through breathing, coughing or sneezing, pathogens may be present in the room air and persist for some time and thus potentially give rise to infections. A typical measure is to disinfect surfaces by wiping them. The disadvantage of this however is that not all areas, surfaces, voids etc. may always be reached and that the process is often very laborious. Furthermore the effectiveness of the wipe disinfection very greatly depends on how thoroughly it is carried out. A completely adequate disinfection may therefore not always be guaranteed in the stressful day-to-day working environment. The use of ultraviolet (UV) light for disinfection is known. Thus, for example patent application US 2012/0126134 A1 proposes that UV radiation emitters be installed on the ceiling and that the radiation be monitored with sensors installed in the room. However, even with this method, it is not always possible to reach all relevant places and surfaces with UV light. This means that many places may only be reached indirectly via reflected radiation or cannot be reached at all.

SUMMARY

The object of the present disclosure is therefore to provide a system that makes possible a disinfection of all relevant surfaces where possible, which at the same time requires as little effort as possible to work and an implementation effort that is as low as possible. This object is achieved by a system for disinfection of surfaces and/or room air as described in the specification and drawings, including the claims.

In accordance with one aspect of the disclosure, a system for disinfection of surfaces and/or room air is provided, wherein at least one UV source is arranged in or on a medical device and/or an item of equipment of a medical examination room and/or treatment room in such a way that it is suitable for disinfection irradiation of at least one surface and/or of at least one flow of air. In this way, e.g. a surface disinfection of the medical device may be carried out. A UV source may for example be a UV LED, a UV lamp, or a fluorescent tube, which is suitable for emitting ultraviolet radiation. The UV source may optionally comprise a lens and/or a baffle, e.g. for deflecting the beam path. For example UV LEDs may be built into cladding, i.e. an outer layer, of medical devices for example. This may be possible relatively simply as a result of the LEDs having a small size and a low power loss. The system may be configured for example to control the at least one UV source with respect of a wavelength employed, a radiation intensity, and/or a mechanical control, e.g. movement control. The UV source may be configured to emit radiation in any suitable wavelength range, e.g. from 100 to 400 nm, 200 nm to 400 nm, 220 nm to 370 nm, etc. UV light is suitable for safely killing bacteria, viruses and/or germs, e.g. mold germs, or for reducing their number. In accordance with one form of embodiment, the UV source may be configured to emit UVC light, i.e. UV light in the wavelength range from 100 to 280 nm, UVC light in the wavelength range from 100 nm to 300 nm, 180 nm to 230 nm, etc. as has been shown, has the advantage of not having any significant damaging effect on skin or eyes. UV light with a longer wavelength, for example 300 nm to 400 nm, by contrast has the property of working with other layer depths or of penetrating deeper into surfaces, and may be intended for example for cleaning contaminations lying deeper, for example also in transparent or absorbent materials such as fabrics, e.g. table covers. Furthermore long-wavelength UV light may be effective in some circumstances with other cell sizes. The latest knowledge has shown that short-wave UVC light may kill viruses and bacteria with no risk to the skin or eyes, since the penetration depth only includes the layers of skin than have died. In accordance with one form of embodiment, the system may be configured to use UVC radiation harmless to people, e.g. in the wavelength range from appr. 200 nm, as continuous irradiation, e.g. also during the use of medical devices. In accordance with one advantageous form of embodiment, the system may be configured to use a number of UV wavelengths at the same time or at different times. Different wavelengths may for example differ in their effect on different bacteria, viruses, and/or germs. For example, the system may also be configured to employ short-wave UVC radiation as permanent illumination or during the use of a device and long-wave and/or more intensive UV radiation, i.e. UV radiation with increased intensity, before and/or after a treatment time. For instance, there may be provision only to employ a longer-wave and/or more intensive UV radiation if no persons are present in the examination and/or treatment room and/or in the area to be irradiated and/or when persons that are present are protected by appropriate protective equipment, for example UV eye protection. Examination and/or treatment rooms are often free of people during breaks in the treatment. With this combination for example a basic disinfection may be achieved during the treatment, while a thorough cleaning or disinfection takes place during the changeover from one patient to the next. The system may for example comprise a timer, which is configured to perform an irradiation for a predetermined time. The timer may e.g. be configured to switch the at least one UV source on or off or to increase or to decrease its intensity. For example, the timer may be configured in such a way that there is UV radiation for a predetermined period of time in each case, e.g. for 10 secs to 5 minutes, 30 secs to 2 minutes, before the examination, during the examination and/or after the examination, etc. It may thus be ensured that on the one hand the duration of the irradiation is sufficiently long to kill germs, viruses and/or bacteria or to reduce their number sufficiently, and on the other hand the lifetime of the UV source may be optimized.

A medical device may be an examination and/or diagnostic device for example. Components that are used for controlling or for the general use of the medical device, e.g. a control unit and/or an operating device and/or mechanically movable components and/or holder components and/or storage means may also be included as components within the framework of the disclosure. For example, the device may involve an imaging device, e.g. an imaging device for diagnostic imaging and/or for therapeutic/interventional imaging. This may be a magnetic resonance tomography unit (MRT), x-ray device, C-arm x-ray device, computed tomography unit (CT), PET device, ultrasound device etc., for example. There may be provision for example for the disinfection of operating elements of such devices. The medical device may also be a treatment device such as e.g. an endoscope, or a dental medicine device such as e.g. a drill or scaler. The medical device is e.g. a device that cannot be immersed in disinfection media or treated in a cleaning disinfection device ("washing machine"), e.g. an electrically operated device. The at least one UV source in this case may either be arranged outside on the medical device and/or integrated into the device. For instance, the UV source may be arranged in such a way that it is suitable for illuminating surfaces in contact with the operator of the device or surfaces in contact with the patient and for reducing the germs, virus, or bacteria numbers there. In addition or as an alternative, the UV source may be arranged in such a way that areas are reached by the radiation that are not able to be reached or are only able to be reached with difficulty with conventional wipe disinfection. It is also possible, through the irradiation of air, to reduce bacteria, viruses, and/or germs in the room air. An item of equipment of a medical examination and/or treatment room may e.g. be a part of room infrastructure or of a mobile hospital structure. The item of equipment, just like the medical device, may be connected for example via a hardware interface and/or a software interface to the UV source and/or to a central system, e.g. a hospital management system. For example, an item of equipment may be a swivel arm, to which for example a medical device may be attached, but which may also be part of the medical device itself, a treatment table or chair and/or a storage container, e.g. of devices, operating elements, and/or medicaments.

The system may be configured e.g. to apply an irradiation time and/or intensity, which may reduce a number of pathogenic germs by a certain predetermined minimum factor, for example at least the factor 10-5. Advantageously, it may make it possible for the system to carry out a disinfection, whereby the number of germs, viruses, and/or bacteria may be reduced without manual work steps such as a wipe disinfection for all surfaces in contact with the operator and/or the patient having to be carried out. Furthermore, in accordance with disclosure, parts of the room, i.e. items of equipment of components of medical devices present, may advantageously be used in this way with little additional effort, to achieve as complete as possible a disinfection of all relevant or desired points of contact.

In accordance with one form of embodiment, the at least one UV source may be attached to a mechanically-movable component used for the purpose of a medical examination and/or treatment. For instance, the system is configured to exploit the mechanical mobility of the components for moving the UV source to irradiate different and/or difficult-to-access surfaces with UV radiation. Mechanically-movable components may be for example a swivel arm, which may be provided for example to hinge out a recording device, a mobile patient bed, and/or a lifting mechanism, e.g. for heavy medical devices. Advantageously existing movement mechanisms of the medical device and/or of the item of equipment of the examination and/or treatment room may thus be utilized so that the UV source may be brought, e.g. explicitly, into suitable positions for disinfection irradiation or to critical surfaces without further movable components being needed. This is advantageous e.g. since most medical devices possess mechanically movable parts or components, e.g. the C-arm in C-arm x-ray devices.

In accordance with one form of embodiment, the at least one UV source may be arranged on a movably arranged x-ray source and/or a movably arranged x-ray detector and/or on cladding of an x-ray device or C-arm system. An x-ray device may basically have different mechanically-movable axes, which e.g. may also be movable automatically. In accordance with the disclosure these movable axes may be used to be able to illuminate larger surfaces or surfaces in shadow with UV light. For example, one or more UV sources may be arranged on a collimator of the x-ray device. The collimator may for example be attached to a ceiling mount, whereby the UV sources may be able to be positioned in such a way that the intended or relevant areas may be illuminated with UV radiation in the course of the disinfection. If the at least one UV source is provided on the collimator, an existing x-ray device may be upgraded by it for example, by the collimator being replaced. In addition or as an alternative, for example further UV sources may be located on a wall mount and/or a ceiling mount. The further UV sources may be provided for example for disinfecting handles that cannot be illuminated by the collimator itself. A C-arm system may comprise a floor mount and/or a ceiling mount for example and/or be designed as a mobile system. For example UV LED strips may be arranged around the x-ray source and/or around the x-ray device detector. As an alternative or in addition, UV sources may be installed or arranged next to the x-ray detector or on or in the cladding of the C-arm. This may for example allow a number of places, for example 3 sides of a table or device, to be illuminated at the same time with UV radiation. For example, this enables the application time and/or the necessary distance, e.g. a trajectory that the UV source must cover, to be reduced. In accordance with one form of embodiment collision sensors may be provided on the C-arm. This, for example, enables mobile devices, e.g. an ultrasound device, to be recognized or located and disinfected with the at least one UV source on the C-arm. For example, the system may be configured, in pauses in treatment, e.g. when the treatment room is free of people, to travel over corresponding trajectories and to carry out a disinfection by means of the at least one UV source. Furthermore, these trajectories may advantageously also be able to be set variably as a function of the examination carried out beforehand. A variable setting may e.g. be provided in respect of the components being used and/or touched for the examination carried out. For example, there may be provision, after a lung image has been recorded, only to disinfect the wall mount. This enables an optimal disinfection to be guaranteed, for example in respect of the duration and/or operation-related wear, and/or as efficiently as possible.

The x-ray device may be a mammography system, for example. The at least one UV source in this case may be arranged on or integrated into the x-ray source or the collimator and/or cladding of the mammography system. For example, the system may be configured to use UVC radiation that is not harmful to people for disinfection. As an alternative or in addition, the system may be configured so that an irradiation takes place when people are at a distance of at least 1 to 3 meters from the device. This may be able to be established for example by a user entry or a sensor. For example, a moodlight option of the mammography system, i.e. the use of calming or distracting light for a patient, may be expanded by a UV option.

In accordance with one form of embodiment, the UV source may be arranged on a wall mount, floor mount, ceiling mount, swivel arm, and/or a cable. These may be an item of equipment of the medical examination and/or treatment room or part of a medical device and are able to be moved manually or preferably automatically, e.g. by electric motors. A cable may be advantageous, e.g. when a high mechanical precision of movement of the UV source is not needed, since it may be implemented relatively easily and at relatively low cost. For example, a plurality of UV sources may be provided on a cable and/or on different cables. A cable may be attached to a swivel arm, for example. The swivel arm may be embodied as a manipulator for example, which is able to be used in one or more directions. The swivel arm and/or cable may for example be part of the ceiling installation or part of a ceiling lamp. For example, the cable may involve an electrically operated cable, which is embodied e.g. to be able to guide the at least one UV source and/or a ceiling light that comprises the UV source or to which the UV source is attached to one or more positions, e.g. for optimal disinfection. In accordance with one form of embodiment the movable UV source or the swivel arm, the cable or a mount may be connected to the medical device and/or to a hospital management system for exchange of information, e.g. via the IoT (internet of things). A ceiling mount and/or a swivel arm that is fastened to the ceiling may be embodied for example to be able to move through a trajectory, e.g. in the form of a 1800 swing, to be able to illuminate all intended surfaces, e.g. of a device, e.g. of a mammography device. With comparatively simple manipulators such as cables and/or swivel arms there may be provision for moving one or more UV sources or mirrors, primarily in treatment pauses, into illumination positions that position the UV light towards the contact surfaces.

In accordance with one form of embodiment, the at least one UV source may be placed or be able to be placed at, on or above an operating device. The operating device may be an operating panel, a joystick, a keyboard, and/or a computer mouse, for example. The at least one UV source may be attached in a fixed position or be movable, e.g. automatically movable. For example, the UV source may be arranged and be able to be moved in such a way that, as part of a disinfection cycle, it is able to be brought into an optimum illumination position at a suitable distance from the respective surface. Elements reflecting UV radiation may additionally be arranged in, on, or above the operating device in such a way that areas in shadow, that no UV radiation may reach, are avoided. Precisely because operating devices are especially frequently handled by users, e.g. often by different users, the possibility of a regular disinfection is especially advantageous here. For instance, since the geometry of the operating devices and/or a certain sensitivity, e.g. in relation to moisture, means that an appropriate and adequate wipe disinfection is not always sensibly possible.

In accordance with one form of embodiment, a light ring may be arranged on a part of an operating device located in an elevated position during use, e.g. a joystick. The elevated position may make possible an optimum illumination of the operating device, e.g. of an operating panel. Fastening it to a joystick for example may make it possible to arrange the UV sources in a similar way to a lamp above the operating elements of the operating device. The light ring may be arranged in such a way that a handle of the joystick or a shaft of the joystick may be irradiated. To this end, the light ring may have a larger diameter compared to the handle.

In accordance with one form of embodiment, the operating device may comprise at least one UV-transparent component. The operating device may for example be a user interface or an HMI (Human-Machine Interface) element. A transparent component may be a panel, e.g. a touch panel, and/or a surface of the operating device. This for example enables the system to be aligned to radiate in UV rays from a rear side or side of the operating device, wherein e.g. an opposite side of the operating device or a surface on the far side of the operating device may also be disinfected. The UV-transparent components may for example be made of quartz glass or borosilicate glass. For instance, the components may be impermeable to visible light, so that the UV sources are not visible to the user. UV-transparent components may make it possible for example to illuminate places by UV backlight or side radiation, which would otherwise be hard to illuminate, e.g. the surface of the joystick or the joystick handle. Transparent operating panels, touch screens and/or monitors, e.g. with invisible diffusers and with side illumination of the UV light, are conceivable.

In accordance with one form of embodiment the system may comprise a support surface, a holder and/or a tunnel for a medical device, wherein the support surface, the holder, and/or the tunnel is equipped with at least one UV source in such a way that a surface of the medical device may be irradiated with said source when put into it or passed through it. The holder may for example be a charging station, e.g. for remote controls, tablets, and/or ultrasound probes, and/or a box or storage container for a medical device or for a component, e.g. an operating unit for a medical device. The UV sources may be supplied with power by battery, for example. The tunnel may have a round or rectangular tunnel shape, but may e.g. also have a very short length, for example in the form of a ring, or have the shape of a passage chamber. For example, the tunnel may be embodied to enable a catheter, an endoscope, a needle, a probe, and/or a capsule to be passed through it, e.g. before it is inserted into an opening in the body. The at least one UV source may be embodied as a ring for example and/or cover a complete tunnel interior. Also conceivable is a UV chamber, in which for example a catheter may be located for unrolling it after opening the sterile packaging. The system may be configured e.g. to activate the at least one UV source when the medical device is laid on the support surface, is laid in the holder, and/or is moved through the tunnel, the latter e.g. directly before a treatment. The tunnel may also be designed for example as in introduction tube for an endoscope. An embodiment as a long tunnel advantageously enables the time for which the UV radiation may act to be increased. In accordance with one form of embodiment, the holder and/or the tunnel may have protective elements at an entrance, which are embodied in such a way that UV light is restricted to the element that is to be moved into the holder or through the tunnel, and e.g. cannot reach the outside. A charging station or box may, for example, have an interface that is designed to read out a device ID and/or to store and/or initiate the disinfection process in the mobile device in a handshake method. The interface of the charging station may be designed, for example, to forward information, e.g. the device ID the disinfection process carried out, to a hospital management system. In accordance with one form of embodiment, the medical device may comprise UV reflectors, which e.g. may be designed to make possible an irradiation with UV rays on the medical device that is as comprehensive as possible. In accordance with one alternative form of embodiment, the UV sources may also be attached to the medical device, wherein reflectors may be arranged on the support surface, the holder, or the tunnel in such a way that the radiation may be reflected back onto the medical device.

In accordance with one form of embodiment the support surface, the holder and/or the tunnel may comprise a sensor for detecting the presence of the medical device and/or of heavy contaminations. The system may for example be oriented so that, as soon as the presence of the medical device is detected by means of the sensor, the UV source is switched on or is switched on for a specific time. For example, the system may also be configured in such a way that when the sensor detects contamination and/or too little reflected light, an alarm and/or a message for a manual cleaning cycle is sent, e.g. via the interface. This may be advantageous when a disinfection by means of UV light is not sensibly possible because there is too much heavy contamination. UV light-reflecting elements may e.g. make it possible for a plurality of locations to be able to be illuminated by UV radiation without any extensive movement of the UV source or a markedly greater number of UV sources being needed.

In accordance with one form of embodiment, at least one UV light-reflecting element, e.g. a mirror element, may be placed or may be able to be placed in such a way as to make it possible to additionally reach areas otherwise shaded from the UV light of the UV source. The at least one UV light-reflecting element may be movable in this case, e.g. movable automatically. In this way for example, on the one hand energy may be saved, since the available radiation may be used more efficiently, e.g. twice by single reflection. On the other hand a reflection of the UV radiation may make it possible to reach otherwise unreachable places or surfaces with the radiation.

As an alternative or in addition, a cover element may be provided with at least one UV light reflecting element and/or at least one active UV source inside it. For instance, the cover element may be mirrored inside. A UV light-reflecting element may be advantageous for example when a medical device that comprises at least one UV source is covered with the cover element and UV rays emitted by the UV source are reflected back onto the device by at least one UV light-reflecting element. The cover element may for example be a movable cover and or a plug-in cover and e.g. be hinged, displaceable, and/or able to be plugged in. The UV light-reflecting elements, e.g. mirrors, may make possible an optimum illumination, while at the same time, by the nature of the cover element, the environment, e.g. people in the vicinity, are protected from the UV light.

In accordance with one form of embodiment, the system may further comprise a sensor unit, which is configured to detect UV irradiation, a radiation dose, and/or the presence and/or position of humans and/or devices and or a macroscopic surface contamination. The sensor unit may e.g. be provided integrated into the device and/or separate from it or as a standalone design. The sensor unit may be used for quality checking for example, e.g. a correct functionality and/or an overall radiation dose may be able to be checked by detection of the UV radiation. The sensor unit may e.g. be an exposure-checking camera, which is embodied to record, to regulate, and/or to document a UV intensity and time. For instance, the sensor unit may be configured to forward corresponding detected data, to a hospital management system, for example. The system may furthermore be embodied for example not to carry out a disinfection cycle if humans are present and/or to carry it out with a lower intensity and/or changed wavelength. On detection of a macroscopic surface contamination, the system may for example be configured to output a message, for example via an interface, e.g. to a user and/or to a hospital management system, and/or to request mechanical cleaning.

In accordance with one form of embodiment the medical device may comprise the following: A plastic comprising carbon black, titanium oxide and/or zinc oxide and/or a UV-protection layer in the form of a film or layer of lacquer and/or a UV-resistant base material such as glass or metal, e.g. in or on the housing or on the cladding of the medical device. An embodiment of this type may make it possible for the medical device or its surface, e.g. a surface to be irradiated, to be especially robust in relation to UV radiation.

In accordance with one form of embodiment, the system may furthermore comprise an interface for display and/or transfer of status information. The interface may be connected to a hospital management IT, a workflow IT and/or room installation control for example and/or be configured to transfer the status information to the hospital management IT, the workflow IT and/or the room installation control. There may e.g. be provision for the disinfection to be documented in the system and/or superordinate hospital management system and optionally be reconciled or synchronized by information exchange, e.g. including an exchange of relevant treatment information. The interface may be configured for example to exchange, disinfection-relevant information, e.g. IoT (Internet of Things) information or medical IoT information with an environment. The environment may for example be other devices, a central organization unit, for example a hospital management system and/or people located in the room or in an adjacent room and who are to be notified by a display. The information may be able to be transmitted for example via wire and/or wirelessly, e.g. via Ethernet and/or Wi-Fi, and or via hardware, e.g. via floating relay. The information may for example relate to the possible presence of people in the room, a current activation of one or more UV sources at that moment, a switching-on or switching-off or one or more UV sources, the presence of a mobile assistance robot and/or of an assistance drone, the request from a mobile assistance robot and/or an assistance drone about the room, e.g. comprising the transfer of geometry data, wherein the geometry data may relate to critical points to be cleaned and/or may have a reference calibration function. Furthermore, there may be a transfer of the disinfection status, for example to the hospital management, e.g. in conjunction with the transfer of the number of examinations carried out and/or the request for cleaning. The interface may further be configured to display a status display, e.g. a warning display, for example via a monitor or a display panel, relating to the operation of UV sources in the respective room and/or outside in an access area. For example, it is possible to display whether the UV operation at the time is harmful to people or may potentially be harmful to people and/or whether UV operation is not active at the time. Furthermore for example an access control, e.g. in the form of a display and/or a closing/opening of the entrance door to the respective treatment and/or examination room may be controlled by means of the status information. This may for example be useful information for the application of UV adhesives. Furthermore, for example further information may be able to be displayed, e.g. presence of an infectious patient, a pandemic status, the request for mobile assistance robot with UV sources, an application of a UV adhesive. The system may, as an alternative or in addition, also be configured to receive information via the interface, for example with regard to the use of a UV adhesive in the room. Advantageously, an interaction between medical device, infrastructure, workflow, work plan, and/or currently known infection risks may be made possible with the interface for example.

In accordance with one form of embodiment, the system may be configured to enable it to be put into an intensive mode with a more intensive UV irradiation. The intensive mode may for example be a pandemic mode, an influenza mode, and/or an infection mode. For example, a risk of infection may differ depending on the season and the system may be organized, at a time of greater risk of infection, e.g. during the flu season, to switch to the intensive mode. It is also conceivable for the system to be configured, with a patient known to be infectious, e.g. detected by a device operator or queried from a central hospital management system, to use the intensive mode after the treatment. The intensive mode may e.g. be optimized to achieve higher reduction in viruses, bacteria, and/or germs. The system may for example be configured, within the framework of intensive mode, e.g. with a high risk of infection, to make a greater disinfection effort, for example by more frequent use of the UV sources and/or by applying a higher intensity of the UV sources and/or by a longer irradiation time and/or by a more frequent changing of filters. For example, the system may be configured, in an intensive mode, to carry out a UV treatment even during an examination. As an alternative or in addition, the system may be configured to carry out a more intensive cleaning after each patient, for example linked to a longer pause time. The system may be configured for example to distinguish between at least two disinfection modes, wherein one mode is an intensive mode and a further mode is a normal mode. Further modes may for example be an additional pandemic mode and/or an additional influenza mode. The pandemic mode and/or the influenza mode may however also already be included in the intensive mode. The normal mode may for example be oriented to an optimization of throughput, i.e. for example a shorter disinfection duration, and/or lifetime.

The system may, in accordance with one form of embodiment, comprise a UV projector for moving over surfaces with UV radiation. The UV projector may for example function like a UV scanner e.g. with Digital Light Processing (DLP) or a technique similar to DLP. An LED matrix is also conceivable. A camera and/or a radar may also be functionally integrated. The system may be configured for example to project UV light onto places at which no operator or patient is, e.g. comparable with an anti-dazzle main beam headlight. The UV projector may e.g. comprise a UV laser. This for example enables a surface scan with high local intensity to be made possible.

In accordance with one form of embodiment, at least one UV source and/or one UV light-reflecting element may be arranged on a drone and/or on a mobile assistance robot, wherein the drone and/or the mobile assistance robot is configured, within the framework of a disinfection cycle, to bring the UV source and/or the UV light-reflecting element into position in such a way that e.g. predetermined surfaces may be disinfected with it by irradiation. The mobile assistance robot may e.g. be a medical assistance robot, which is oriented for example to be employed in medical environments. Mobile may mean e.g. that it is equipped with rollers for example, and is able to be moved over the floor, e.g. independently of other medical devices. The at least one UV source may for example be attached in cladding elements and/or in or on a manipulator, for example a grip arm or a swivel arm. As an alternative or in addition, the assistance robot and/or the drone may be designed to receive a UV source from a parked position. For example, the assistance robot may comprise a movable robot arm. The assistance robot may grip the UV source or the mirror for the disinfection e.g. with the movable robot arm, i.e. put down an instrument that it has been holding previously and pick up the UV source or the UV light-reflecting element (tool change). The movable robot arm may for example allow flexible operating elements, clamps, detectors, tables and/or under tables etc. to be irradiated with UV. For example, there may be provision during and/or after and/or before an operation to disinfect operating equipment and/or the operating area. The system may e.g. be designed to carry out a disinfection in treatment pauses, e.g. when nobody is in the room, and/or request a mobile assistance robot for this purpose. For example, the system may be designed to carry out a calibration, in that coordinates of the medical device and of the respective room are exchanged with the drone and/or the mobile assistance robot. For example, the drone and/or the assistance robot may have autonomous navigation. The autonomous navigation may for example be a map, e.g. a 3D map, which may be designed for example so that manually critical areas may be marked. As an alternative or in addition, a sensor interface may be provided. For example, the medical device may have sensors and may be configured to give feedback to the drone or to the assistance robot, for example via reflectors, which may be evaluated with a camera and/or a sensor in the drone or the assistance robot and which make possible a spatial encoding, wherein for example a calibration of the coordinate system may be made possible by means of the spatial encoding.

In accordance with one form of embodiment, the mobile assistance robot and/or the drone may be configured to pick up a dry vacuum cleaner, wet vacuum cleaner, and/or a blower, e.g. a warm-air blower from a parking position and use it for cleaning at least one surface. The assistance robot and/or the drone may be embodied for example, with the aid of air flow, to blow or to suck germs, viruses, and/or bacteria from inaccessible places in areas that may be irradiated with UV light. Cleaning with a dry vacuum cleaner, wet vacuum cleaner, and/or a warm-air blower or blower may for example make it possible to clean off contaminations that cannot be dissolved with UV radiation, for example on support surfaces, operating panels and/or handles, e.g. in the form of dirt or body fluids.

In accordance with one form of embodiment, the mobile assistance robot and/or the drone and/or a blower that may be picked up, e.g. a warm-air blower, may have contactless temperature measurement available and may be configured to record a temperature-time integral and/or temperature peak values. The temperature measurements may be used for example as a quality check. As an alternative or in addition, sensor elements with an IoT interface may be located in the components to be cleaned. These may be designed for example to carry out a temperature measurement and forward it via the interface.

In accordance with one form of embodiment, the system may comprise a parking and charging station for the mobile assistance robot and/or the drone. For instance, the parking and charging station may comprise UV radiation reflecting elements and/or UV sources, which are designed for a disinfection of the assistance robot and/or the drone. The parking and charging station for the drone may be accommodated for example on a wall mount, a magnet and/or a gantry with a defined mechanical and/or electronic interface. The parking and charging station may for example comprise a mechanical and/or electronic interface, which is configured to synchronize the coordinates of the medical device with a coordinate system of the drone. With mobile medical devices e.g. the parking and charging station for the drone may comprise a transport holder. For example, the parking and charging station may comprise a UV source, wherein the assistance robot is configured to take hold of the UV source and illuminate itself by means of a grip arm and/or manipulator. The parking and charging station may for example comprise an interface, e.g. to a hospital management system, wherein the system may be oriented for the utilization of the parking and charging station to be able to be planned and logged with a central facility, e.g. the hospital management system. The parking and charging station may for example comprise Bluetooth, NFC, a camera for uniquely identifying the current device, etc. In accordance with a detection of the current device e.g. device-specific disinfection parameters may be loaded. The assistance robot may for example be configured to take medical components, of medical devices for example, with it to its parking and charging station and to disinfect these, e.g. with the aid of its manipulator or grip arm, but also by placing them on support surfaces correspondingly provided. Further mobile devices, for example ultrasound heads, may be disinfected in this way in the parking and charging station. If the parking and charging station contains reflecting elements, the assistance robot and/or the drone may be oriented for example to disinfect themselves with their own at least one UV source. In accordance with one form of embodiment the parking and charging station may be able to be closed, e.g. in a UV-tight manner. An ability to be closed in a UV-tight manner may be made possible for example with a door or a curtain.

In accordance with one form of embodiment, the system may have a means for creating flows of air, which is designed to suck or to blow germs, viruses, and/or bacteria into an area able to be irradiated with UV radiation. The means for creating flows of air may for example be part of a ventilation system of a medical device. Advantageously the room air may be circulated with this and e.g. germs in the air in shaded areas may also be captured with this. For instance, since pathogens such as for example Coronaviruses in the room air cannot multiply, the number of germs or viruses in the room may thus advantageously be reduced. Advantageously, one or more UV sources may be arranged in such a way that a sufficiently long irradiation, for example in a period ranging from 5 seconds to 5 minutes, may be made possible to achieve a biocide effect. For example, a UV-illuminated labyrinth channel and/or a cyclone system, in which e.g. the fan and the cyclone are on the exhaust side, and/or a HEPA filter may be part of the system. In addition or as an alternative for example, in conjunction with operating elements and/or openings for people, e.g. tunnels and/or bores in medical devices, a creation of flows of air may be implemented. In accordance with one form of embodiment the means for creating flows of air may be an air cooling system with an air cooler and the area able to be irradiated with UV radiation may be located in or on the air cooler. In this case e.g. a cool air circulation of the medical devices, e.g. in/around a tunnel and/or in/around the bore(s) may be provided for a reduction of viruses bacteria and/or germs in the treatment room. Bore in this context refers to the tubular examination area of an imaging device such as e.g. MRT or CT.

In accordance with one form of embodiment, the system may comprise at least one UV source, which is arranged in and/or on an examination area of a medical imaging device.

Devices for medical imaging may for example be magnetic resonance (MR), Positron Emission Tomography (PET), and/or Computed Tomography (CT) devices. Some of these use bore lighting or lighting for the examination area for psychological and/or design reasons. The UV source may for example be connected to or integrated into such lighting. For instance, the at least one UV source may be in the same position as the visible lighting. As an alternative or in addition, however, a UV source or a number of UV sources may also be attached at other positions, e.g. at more positions. It is also conceivable for the system to be designed for a UV source, which for example obtains its power from a local coil supply or a battery, to be placed on the table during pauses in treatment. Large devices with a patient table may for example also be equipped with a mirror. The at least one UV source may for example be placed on the wall or on the device on a holder. For example by a movement of the table the mirror may be moved into the examination area so that all necessary surfaces are illuminated and disinfected.

In addition or as an alternative, the system may comprise examination area ventilation, wherein the examination area ventilation comprises an air channel in which UV sources for irradiating the air flowing through said channel are arranged. Optionally, at its exit to a patient area, a HEPA filter may additionally be arranged for filtering the flow of air. It is known that a few viruses, for example Coronaviruses, may survive for a longer time in the air. Since in a few scenarios a patient is located for a longer time in the examination area, ventilation of the examination area may be provided for example moving centrally outwards and/or from the flow in or against the alignment of the patient. Such an implementation may be provided for example in stationary devices such as CT gantries and/or MR devices with bore ventilation or examination area ventilation and/or angiography systems. In addition or as an alternative, an implementation may be provided in mobile medical devices, such as e.g. ultrasound devices and/or C-arm devices. The air channel may for example be an air circulation channel with which the UV radiation of the UV source makes it possible to remove germs from the air and free it from viruses and bacteria. The HEPA filter may for example be an H13 or H14 filter. The use of a cyclone system is also conceivable, which may be applied to save space. In this case the cyclone chamber may likewise be able to be irradiated by means of UV sources UV and/or may additionally be coated with a biocide, for example with silver ion. In addition, further controllable UV sources may be provided, which cannot be able to be reached by a conventional illumination of the examination area. For example, there may be a control of the illumination and/or of the ventilation by the medical device, a room control or a higher-ranking control level, for example the hospital management system or a hygiene management system.

In accordance with one form of embodiment, the system may be designed to irradiate the area underneath a table, e.g. a treatment table. The underside of medical tables, for example operating tables, is in many cases not part laminar air flow. A UV illumination on the underside of the table may advantageously be used here to reduce the number of germs, viruses, and/or bacteria there. This may for example have advantages when parts of an imaging device must move to or remain here during a recording.

A further aspect is a drone comprising a UV source, which is arranged on the drone in such a way that it is suitable for mobile disinfection irradiation of surfaces, wherein the drone is configured to bring the UV source into position in such a way that it may disinfect, e.g. predetermined surfaces through irradiation. All advantages and features of the system for disinfection also apply by analogy to the drone and vice versa.

A further aspect is a method for disinfection of surfaces and/or room air, wherein at least one UV source is moved by means of mechanically movable components for the purpose of the medical examination and/or treatment to irradiate different and/or difficult to access areas. All advantages and features of the system for disinfection also apply by analogy to the method, and vice versa.

In accordance with one form of embodiment of the method, the movable components and the UV source may be put into a disinfection mode in a first step by a user entry or triggered by a predetermined event, comprising the switching on of the UV source for even or variable emission of UV radiation, wherein the UV source, in a second step, may be moved automatically based on a predetermined movement pattern and/or based on sensor data detected by a sensor unit. This following of a predetermined movement pattern by the UV source with specific intensity is also referred to as a "hygiene program." For example, a mechanically-movable component of a medical device, e.g. a compression pad, may be moved to a predetermined height, e.g. a height that allows at least one predetermined surface to be irradiated with UV light. For example UV light emitted from a UV source from a collimator area and/or the compression unit may irradiate predetermined surfaces, e.g. contact surfaces. For instance, by using a mechanical hinge, e.g. of a tomography device or a C-arm, the surface, e.g. a surface under the compression pad, may be optimally illuminated. In addition or as an alternative a further UV source, e.g. under an (x-ray) detector may irradiate another surface, e.g. the underside of the detector cladding.

In accordance with a further aspect, the disclosure is also directed to a method for controlling a system, wherein the system comprises a medical examination and/or treatment area. All advantages and features of the system and method for disinfection also apply by analogy to the control method. The control method comprises the steps:

detecting whether a patient is located in the examination and/or treatment area;

if no patient is located in the examination and/or treatment area, carrying out a hygiene program by means of the UV source;

after conclusion of the hygiene program, transferring a disinfection state to a hospital management system (Hospital Information system, HIS).

The examination area may for example be the bore of an examination device (e.g. MRT or CT), or the table or the standing area of an x-ray device. Typically, an examination or treatment is first performed on a patient in the examination or treatment area. When this is at an end the system checks, by means of infrared sensors for example, whether the patient is still located there. The system then switches into the disinfection mode and a e.g. predetermined hygiene program is carried out. In a few forms of embodiment this may be at least partly carried out when the patient is still located in the examination area. In this case the UV dose that the patient has received is also transferred to the HIS, so that for example the UV radiation may be switched off if a highest dose is exceeded. In accordance with one form of embodiment different hygiene programs are available, e.g. a normal hygiene program for an average protection against viruses and bacteria, a mid-strength hygiene program for stronger protection, e.g. at flu time, and a hygiene program with maximum protection, e.g. for fighting multi-resistant germs. The hygiene programs differ e.g. in their duration and/or in the intensity of the UV radiation. Further, after conclusion of the cleaning program, a disinfection state is transferred to the HIS, which may for example also include the strength of the hygiene program. This method may be carried out automatically. It is further possible for the disinfection state to be displayed at the medical device or in the examination or treatment room, so that the medical personnel know when the next patient may enter the examination or treatment area.

BRIEF DESCRIPTION OF THE DRAWINGS/FIGURES

The characteristics, features and advantages of this disclosure described above, as well as the manner in which these are achieved, will be explained more clearly and easily understandably in conjunction with the description of the exemplary embodiments given below, which will be explained in greater detail in conjunction with the drawings. In the figures.

DETAILED DESCRIPTION

Figure 1:
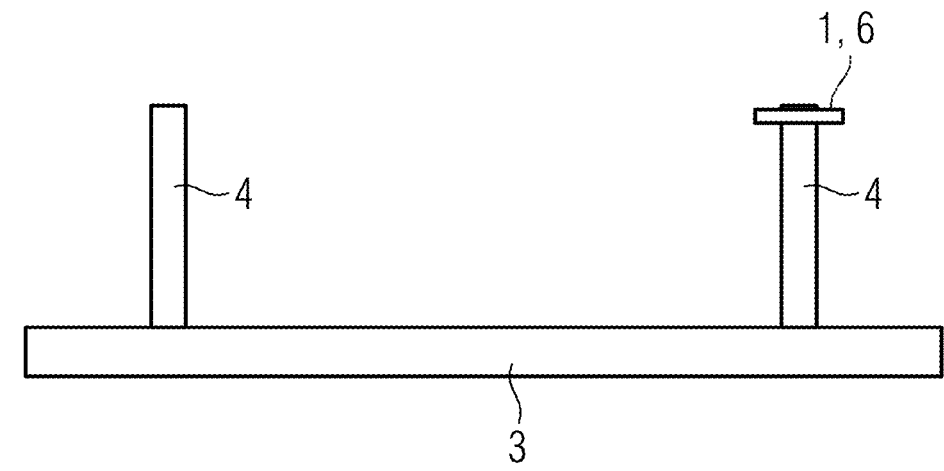
FIG. 1 shows an operating panel with two joysticks, wherein a UV light ring is fastened to one of the joysticks, in accordance with one or more embodiments of the disclosure.

FIG. 1 shows an operating panel 3 with two joysticks 4. A UV source 1 in the form of a UV light ring is fastened to one of the joysticks. In this form of embodiment, the UV light ring 6 has a much greater diameter than the joystick 4, thereby extending laterally beyond it. For instance, the joystick 4, in combination with UV light ring 6, may have the shape of a UV mushroom. This e.g. makes it possible to illuminate the entire joystick, e.g. the handle of the joystick 4, with UV light. Furthermore, the UV light ring 6 may also illuminate parts of the operating panel 3. An illumination of the other joystick is at least partly possible. As an alternative, the UV light ring 6 may also have a smaller diameter, e.g. a diameter that approximately corresponds to the diameter of the joystick 4. This may be advantageous for ergonomic reasons for example. Also conceivable, for example, is an upper screen above the UV light ring 6, which may be fastened directly to the UV light ring 6 for example and which may prevent radiation upwards, so that a user is not directly subjected to the radiation, e.g. when UV light is to be emitted during the use of the operating panel 3. Thus, the UV light ring may be used in continuous operation or at least for longer times (e.g. 10 minutes each hour), e.g. when it is emitting UV light harmless to human beings. What is described here and in the figures below with regard to an operating panel 3 may also be transferred to other surfaces of medical devices 25, e.g. surfaces reachable for operating personnel. For example, the operating panel 3 may be replaced by a couch with handles instead of the joysticks 4 and otherwise be constructed in a similar way.

Figure 2:
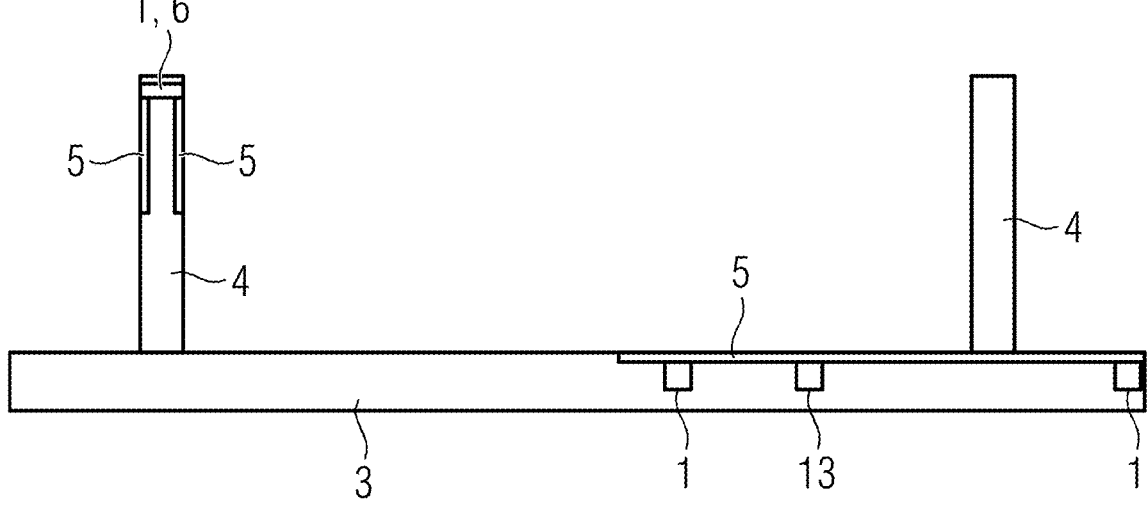
FIG. 2 shows an operating panel with two joysticks which comprises UV-transparent components, in accordance with one or more embodiments of the disclosure.

FIG. 2 shows an alternative form of embodiment of an operating panel 3 with two joysticks 4, which comprises UV-transparent components 5. In this form of embodiment, one of the joysticks has a light ring 6, which has a diameter that approximately corresponds to that of the joystick 4. The joystick moreover has UV-transparent components 5 on its sides, which e.g. makes possible an irradiation of the surface of the joystick handle. The UV-transparent components 5 advantageously allow a blind spot to be avoided in which there cannot be any irradiation. In this way viruses, bacteria, and/or germs on the surface of the UV-transparent components be reached especially easily by the radiation. In this form of embodiment, only a part of the outer surface of the joystick 4 is provided with the UV-transparent components 5. It is however conceivable to provide a larger portion of the outer surface or even the entire outer surface therewith, to make possible a maximum possible transparency for UV light.

Figure 3:
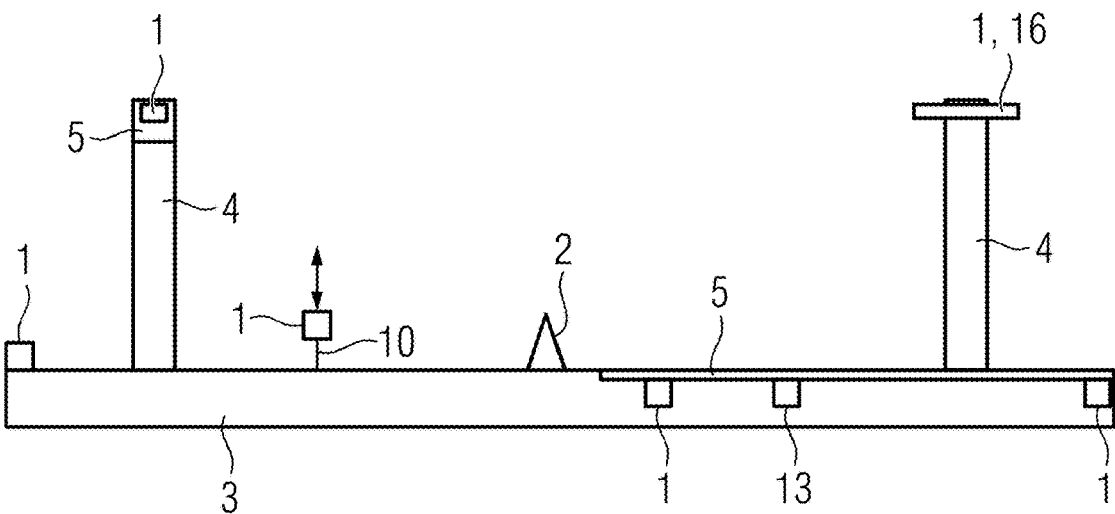
FIG. 3 shows an operating panel with a UV source adjustable by a movable mount, two joysticks, UV-transparent components and a UV light-reflecting element, in accordance with one or more embodiments of the disclosure.

The other joystick 4 here, corresponding to the form of embodiment in FIG. 3, has a UV light ring 6 with a greater diameter. The different variants are basically able to be swapped and/or combined in any given way within an operating panel 3. Furthermore, in this form of embodiment, the operating panel 3 also has a UV-transparent component 5. Located behind the UV-transparent components 5 are two UV sources 1 and also a sensor unit 13, which may serve to detect a radiation power. Thus, for example an insufficient irradiation because of heavy dirt or objects lying in the way, may be detected. On the other hand, by detection of the overall dose, the duration of the use of the UV sources may be explicitly controlled. The UV-transparent components 5 in this case allow the UV sources 1 and the sensor unit 13 to be arranged in a space-saving manner and without any disruption, while a comprehensive illumination is still possible. The operating panel 3 may be covered partly, as shown, but also completely or almost completely with the UV-transparent components 5. Of course it is also conceivable for only the operating panel 3 or only one joystick 4 to comprise UV-transparent components 5.

FIG. 3 shows a further form of embodiment of an operating panel with a UV source 1 adjustable by means of a movable mount 10, two joysticks 4, UV-transparent components 5, and a UV light-reflecting element 2, as well as further UV sources. In the form of embodiment, a UV source 1 is also arranged on the operating panel. The adjustability of the one UV source 1 (visually indicated by the arrows), the UV light-reflecting element 2 and the UV-transparent components 5 make possible an extremely comprehensive irradiation of the operating panel 3 with UV light. One joystick 4 for its part has a UV light ring 6. The other joystick 4 on the other hand has an integrated UV source 1 inside it that, thanks to the UV-transparent components 5, may radiate UV light into the environment or onto surfaces in the environment. The individual components shown here may basically be combined in various ways, e.g. as required in accordance with the arrangement of surfaces to be reached.

Figure 4:
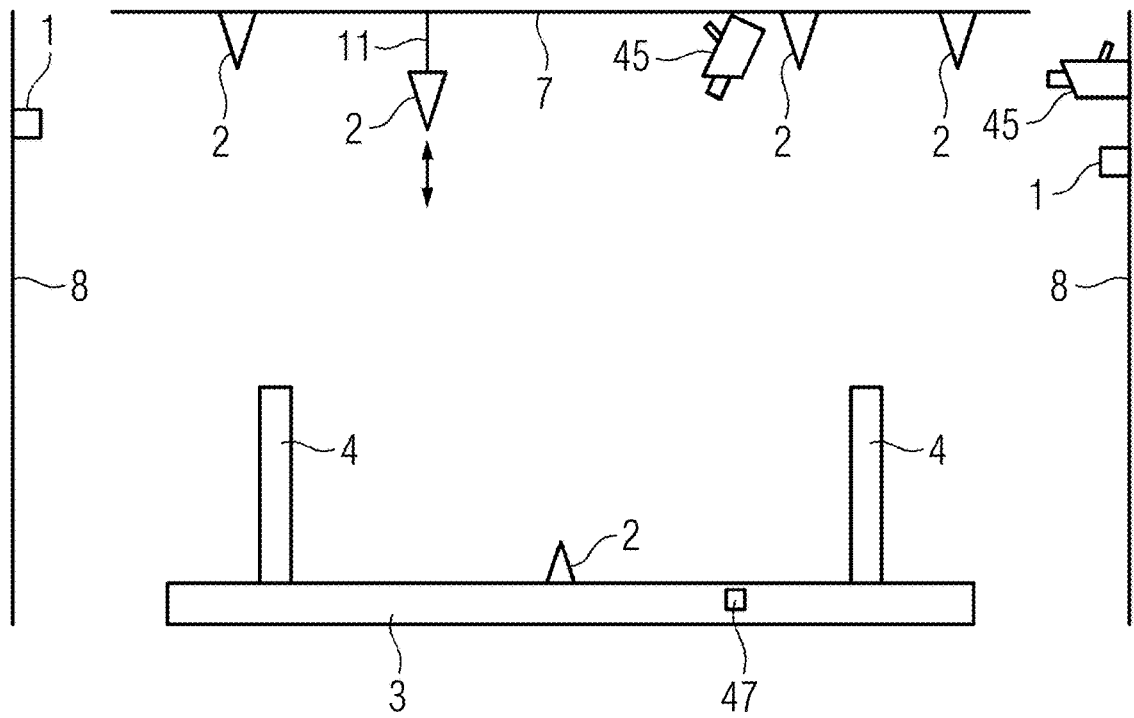
FIG. 4 shows an operating panel with a UV light-reflecting element, which may be irradiated by UV sources fastened to walls, in accordance with one or more embodiments of the disclosure.

FIG. 4 shows an operating panel 3 with two joysticks 4 and a UV light-reflecting element 2. In this form of embodiment, the operating panel 3 itself does not have any UV sources 1, but is irradiated by UV sources 1, which in this case are fastened to walls 8. The UV light-reflecting element 2 e.g. serves to let UV light reach all relevant points. For example, in this way the sides of the handles of the joysticks 4 may be irradiated in the optimum way. Located on the ceiling are further UV light-reflecting elements 2, which e.g. serve to divert the UV rays onto the operating panel 3. One of the UV light-reflecting elements 2 in this case is fastened to a cable 11 and is thus height-adjustable. This allows an even more flexible adaptation of the beam path, e.g. even with components to be irradiated of which the location changes. Irradiation control cameras 45 serve to monitor the radiation dose applied. A reflection surface 47 may serve as reference in this case. As an alternative, instead of the reflection surface, a control stamp may also be used, e.g. in the form of a gel, which is deactivated by UV. In this form of embodiment the operating panel 3 may also be replaced by another surface of a medical device 25. A configuration of this type is basically suitable for irradiating different types of surfaces.

Figure 5:
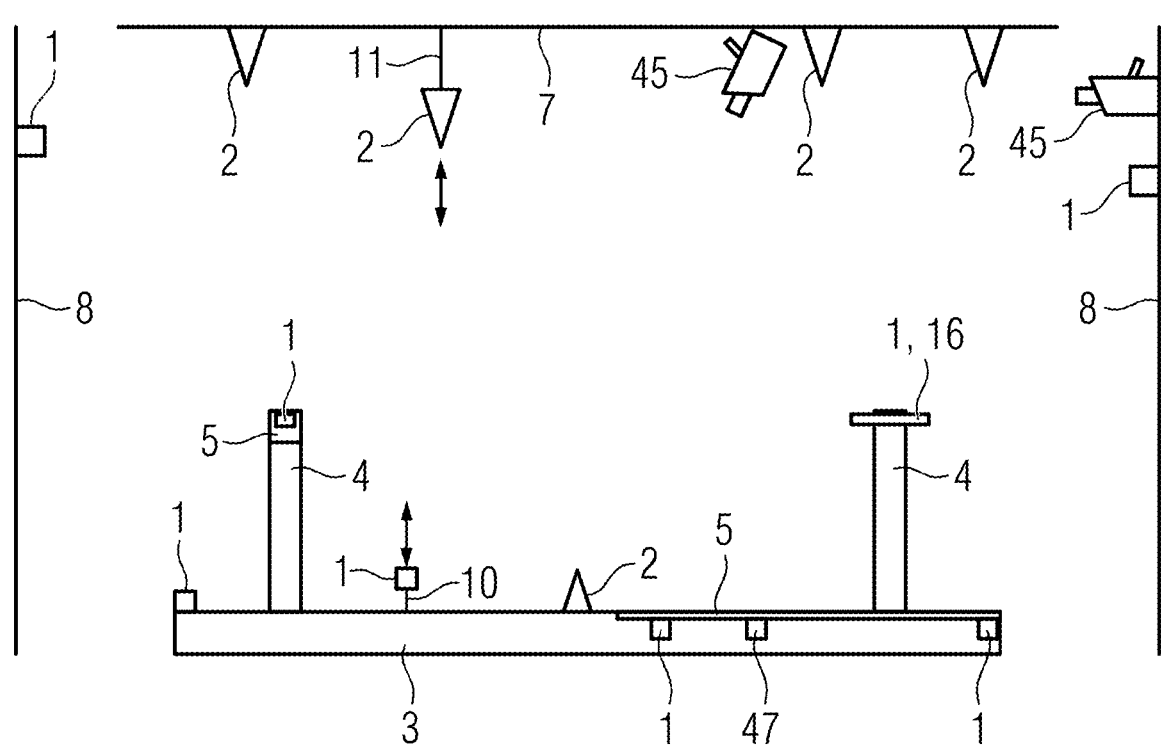
FIG. 5 shows an operating panel with a few UV sources, similar to those in FIG. 3, in combination with UV sources and UV light-reflecting elements fastened to the ceiling and to the walls, similar to in FIG. 4, in accordance with one or more embodiments of the disclosure.

FIG. 5 shows a form of embodiment in which an operating panel with its own UV sources 1, similar to that shown in FIG. 3, in combination with UV sources and UV light-reflecting elements 2 fastened to the ceiling and to the walls, in a similar way to in FIG. 4, is depicted. This form of embodiment allows an especially thorough and comprehensive disinfection. For instance, it is conceivable for even further surfaces of further medical devices 25 to be disinfected as well.

Figure 6:
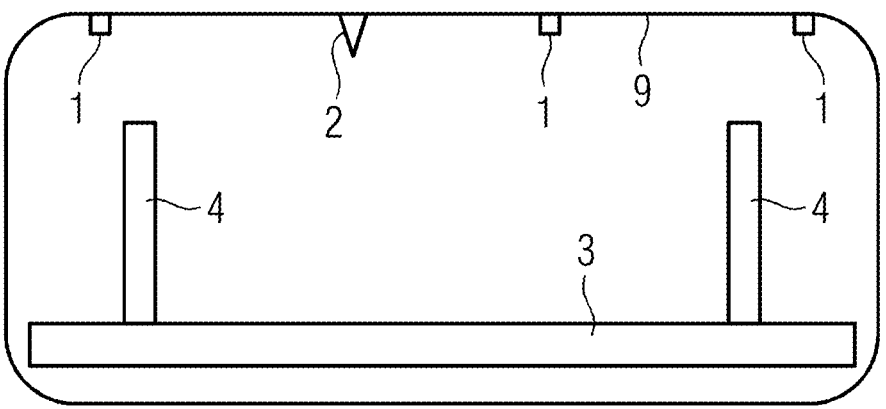
FIG. 6 shows an operating panel, which is covered by a cover comprising UV sources, in accordance with one or more embodiments of the disclosure.

FIG. 6 shows an operating panel 3, which is covered by a cover 9. The cover 9 surrounds the operating panel 3 completely in this case. The cover 9 comprises a number of UV sources 1 that, when the cover 9 surrounds the operating panel 3, may be used for disinfection of the operating panel 3. The cover in this example surrounds a UV light-reflecting element 2, which ensures a better spread of the UV rays or a more comprehensive irradiation of the operating panel 3. Basically, a number of UV light-reflecting elements 2 may also be used, e.g. UV light-reflecting elements 2 may also be provided on the operating panel 3 itself.

Figure 7:
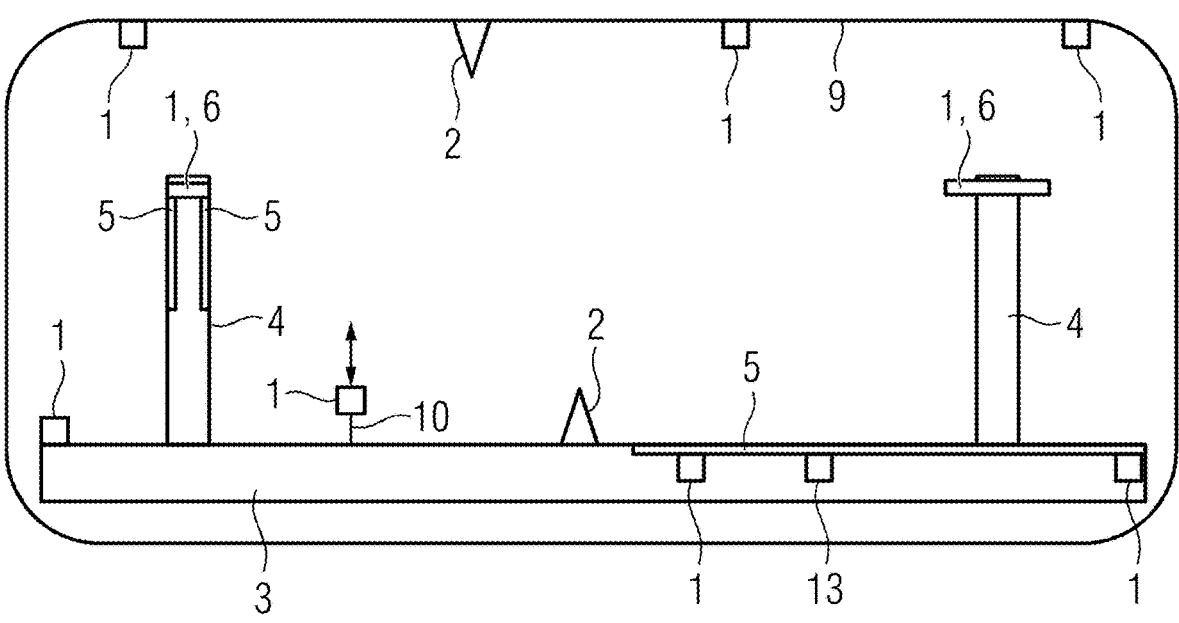
FIG. 7 shows an operating panel which is covered by a cover, wherein both the operating panel and also the cover comprise UV sources and UV light-reflecting elements, in accordance with one or more embodiments of the disclosure.

FIG. 7 shows an operating panel 3, which is covered by a cover 9, wherein both the operating panel 3 and the cover 9 include UV sources 1 and UV light-reflecting elements 2. Here too the operating panel 3 comprises two joysticks 4, each with a UV light ring 6, wherein one joystick 4 comprises a light ring 6 of a greater diameter, while the other joystick makes possible a better distribution of the UV light with UV-transparent components 5. The operating panel 3 furthermore likewise comprises, like the version in FIG. 3, UV-transparent components 5, an adjustable UV source 1 on a mount 10 and a sensor unit 13.

Figure 8:
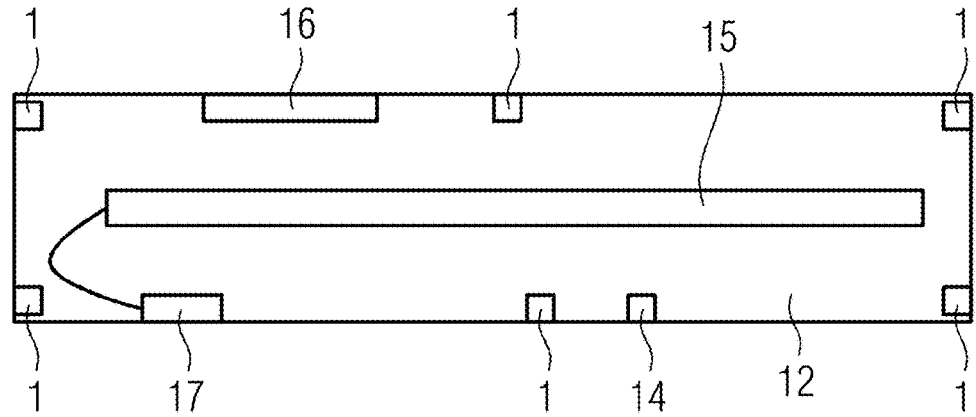
FIG. 8 shows a side view of a storage box with UV sources for a component of a medical devices, in accordance with one or more embodiments of the disclosure.

FIG. 8 shows a view from above of a storage box 12 with UV sources 1 for a component 15 of a medical device. The component 15 may for example be a remote control, a key, a trigger, a detector, a grid, or a tablet, which is used for control and/or evaluation. A number of UV sources on the walls of the storage box 12 serve to disinfect the component 15 when said component is located in the storage box 12. The component may be charged by means of a charging station, where the component 15 involved is a component that requires power. An interface 16 may serve to recognize or identify the component, e.g. via RFID, NFC, barcode, IoT, etc., and synchronize the component with a central unit, via wire or wirelessly. For example, it is possible to implement a quality check in this way. A sensor 14 may on the one hand be organized to detect the presence of the component 15 and on the other hand to detect and measure the UV radiation.

Figure 9:
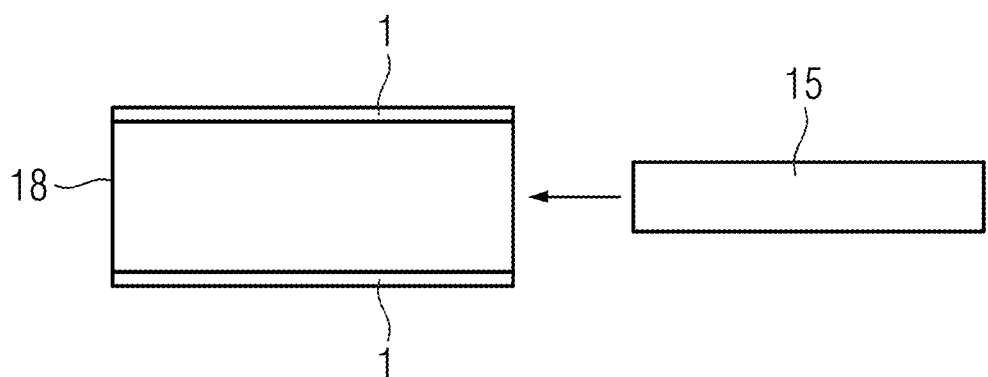
FIG. 9 shows a side view of a container for a component of a medical device, in which UV sources are arranged along the entire length of two side walls, in accordance with one or more embodiments of the disclosure.

FIG. 9 shows a side view of a holder 18 for a component 15 of a medical device, in which UV sources 1 are arranged along the entire length of two side walls. This arrangement of the UV sources may guarantee a fully comprehensive disinfection, e.g. even when the component 15 is arranged at a small distance from the side walls.

Figure 10:
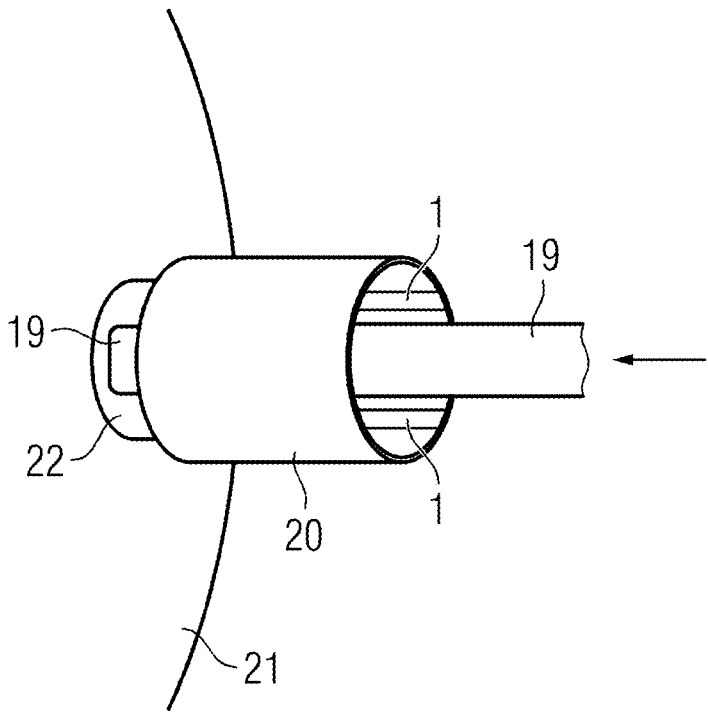
FIG. 10 shows a perspective view of a tunnel for an endoscope in which UV sources are arranged, in accordance with one or more embodiments of the disclosure.

FIG. 10 shows a perspective view of a tunnel 20 for an endoscope 19 in which UV sources 1 are arranged. The tunnel is designed to be placed directly on a body opening 22 of a body 21, so that the endoscope 19 may be disinfected with UV light in the tunnel 20 before being introduced into the body 21.

Figure 11:
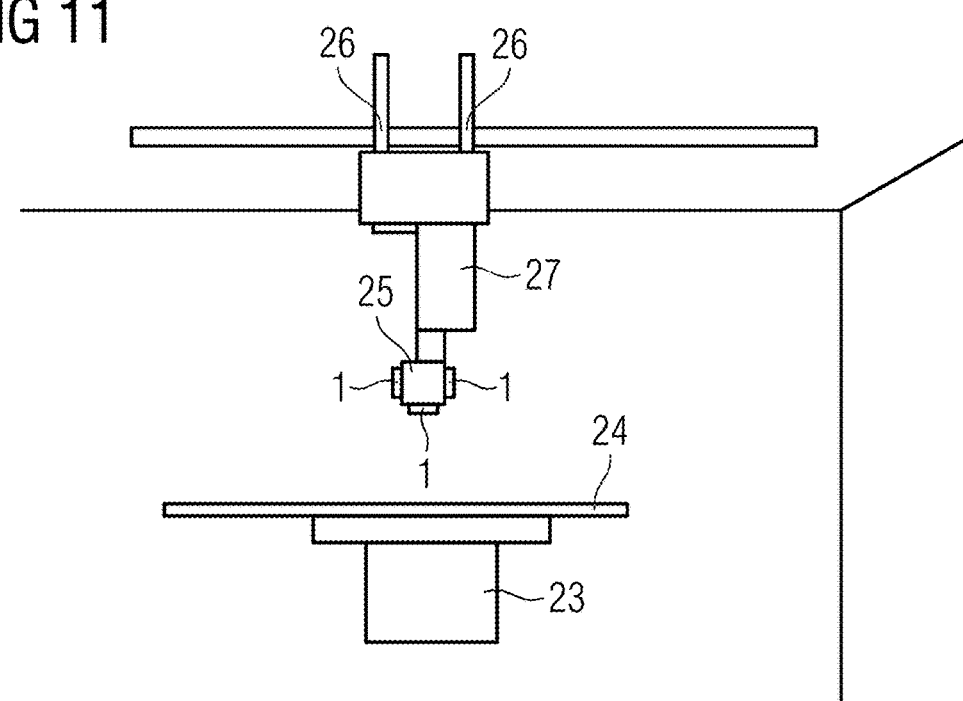
FIG. 11 shows a patient couch, above which a medical device is placed, which is movable by means of a swivel arm, wherein UV sources are arranged on the medical device, in accordance with one or more embodiments of the disclosure.

FIG. 11 shows a patient couch 24, which stands on a pedestal 23 and above, which a medical device 25, e.g. an x-ray device, is placed. The medical device 25 is movable by means of a swivel arm 2, and UV sources 1 are arranged on the medical device 25. The medical device 25 may optionally be fastened via rails 26 to the ceiling, whereby an even greater flexibility or mobility of the medical device 25 and thus also of the UV sources 1 may be achieved. The mobility of the medical device 25 and of the UV sources 1, e.g. through the swivel arm 27, enables a flexible illumination of the patient couch 24 and where necessary also of other surfaces to be made possible. The UV illumination may be provided in operating pauses for example, in which for example the swivel arm 27 moves in accordance with a predetermined movement pattern over the relevant and reachable contact surfaces, e.g. the patient couch 24, and disinfects them by means of the UV sources 1.

Figure 12:
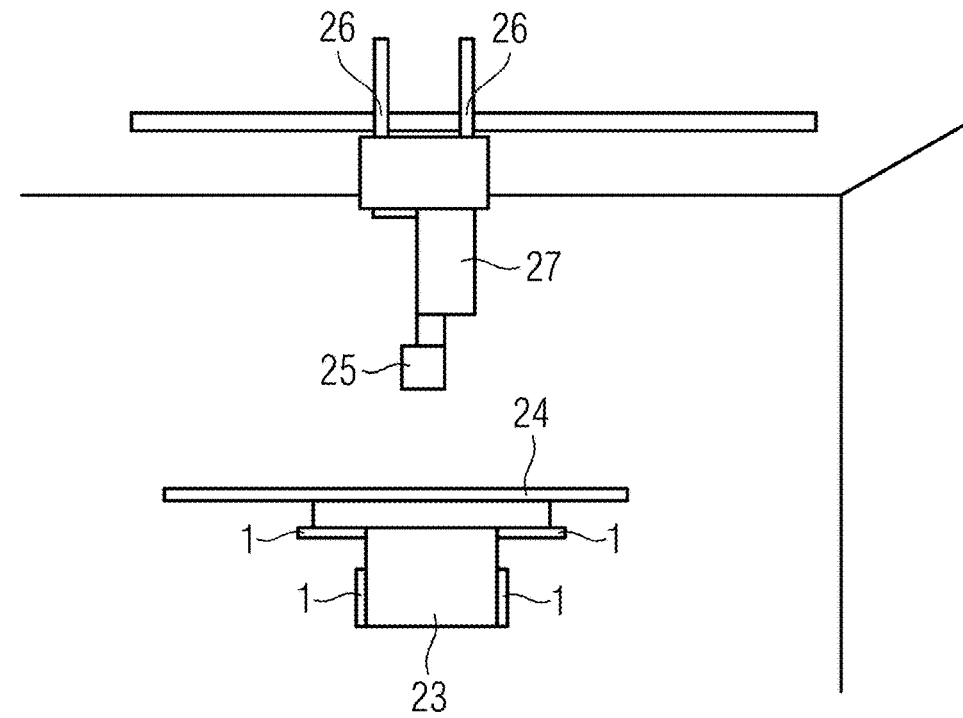
FIG. 12 shows a patient couch, wherein UV sources are fastened directly to an underside of the patient couch and to its pedestal, in accordance with one or more embodiments of the disclosure.
Figure 13:
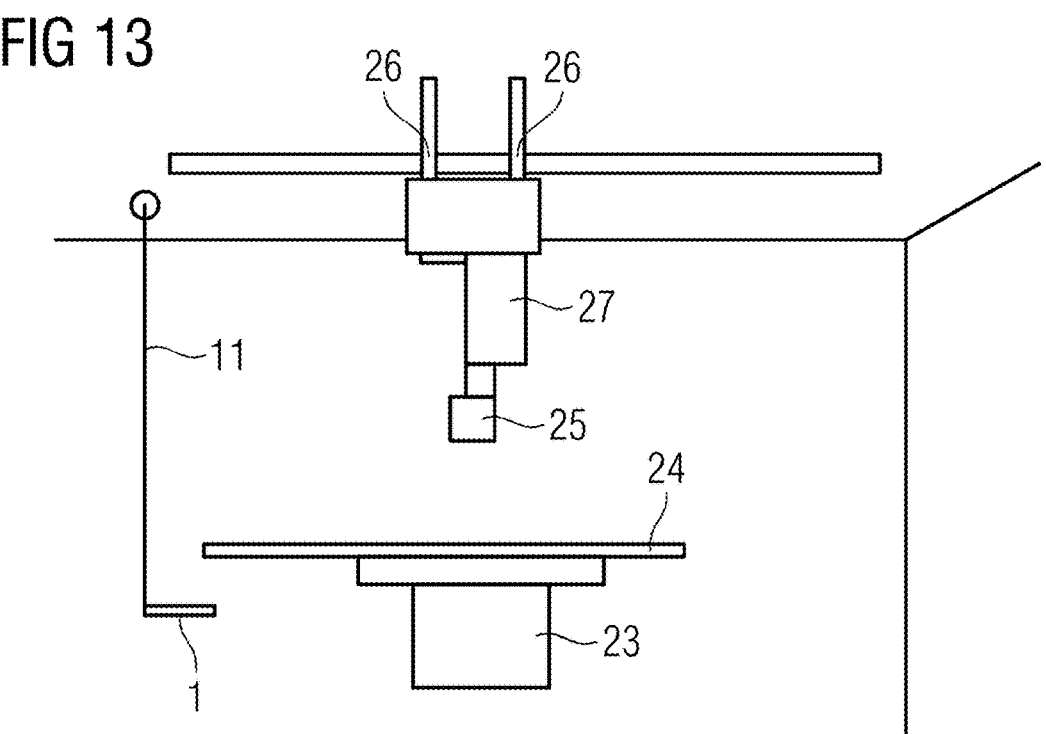
FIG. 13 shows a patient couch, above which a medical device is placed, wherein a UV source is arranged height-adjustably by means of a cable in order to irradiate the patient couch and/or the medical device with UV light, in accordance with one or more embodiments of the disclosure.

FIG. 12 shows an alternative form of embodiment, in which the UV sources are fastened directly to an underside of the patient couch 24 and to its pedestal 23. Thus, an especially effective illumination, e.g. also below the patient couch 24, may be made possible. In FIG. 13 on the other hand a cable 11 is provided, which makes possible a height-adjustable arrangement of a UV source 1 fastened to the cable 11. This enables surfaces of the medical device 25 and of the patient couch to be flexibly irradiated with UV light. A combination of two or all three forms of embodiment of FIGS. 11-13 is likewise conceivable in order to make possible an especially effective illumination and disinfection.

Figure 14:
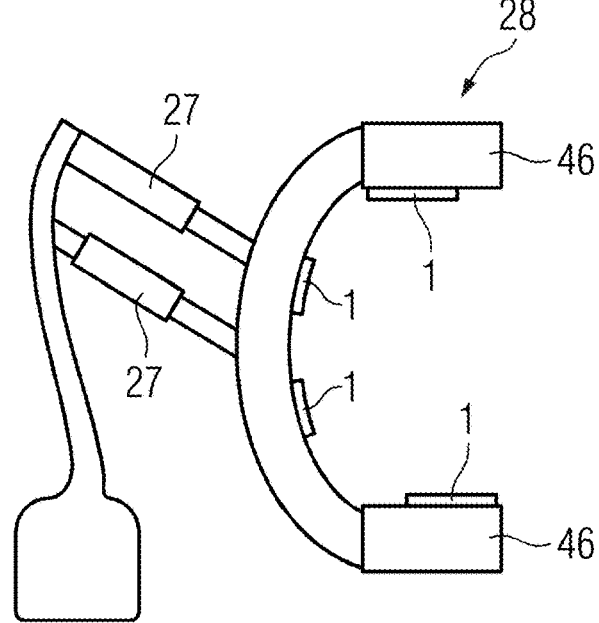
FIG. 14 shows a C-arm system with x-ray source and x-ray detector, which is movable by means of two swivel arms and has UV sources inside the C-arm, in accordance with one or more embodiments of the disclosure.

FIG. 14 shows a C-arm system 28 with x-ray source 46 and x-ray detector 46, which is movable by means of two swivel arms 27. Arranged on the x-ray source and detector 46 and also inside the C-arm are UV sources, which make possible a disinfection by UV radiation. The mobility of the C-arm system 28 thus explicitly enables surfaces to be selected and disinfected during pauses in examination.

Figure 15:
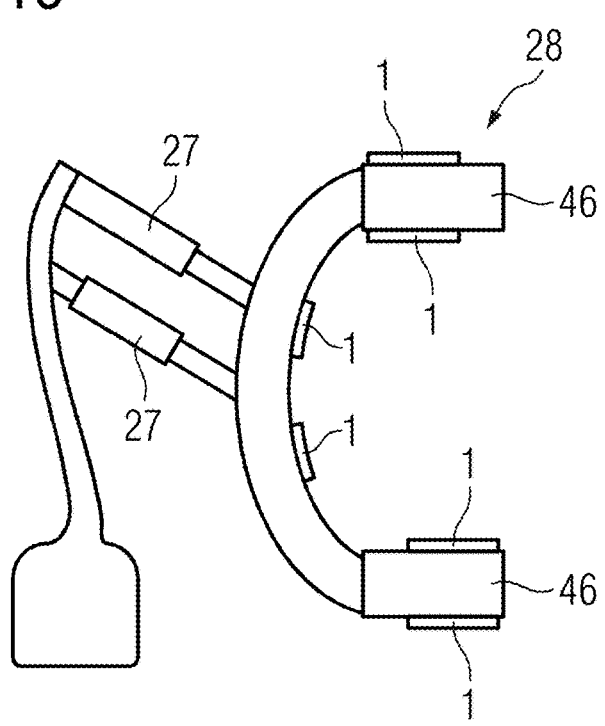
FIG. 15 shows a variant of the C-arm system from FIG. 15, in which further UV sources are arranged on an outer side of the C-arm, in accordance with one or more embodiments of the disclosure.

In an alternative form of embodiment, shown in FIG. 15, further UV sources 1 may also be arranged on the inner sides of the C-arm, whereby advantageously even further surfaces are able to be reached by UV light.

Figure 16:
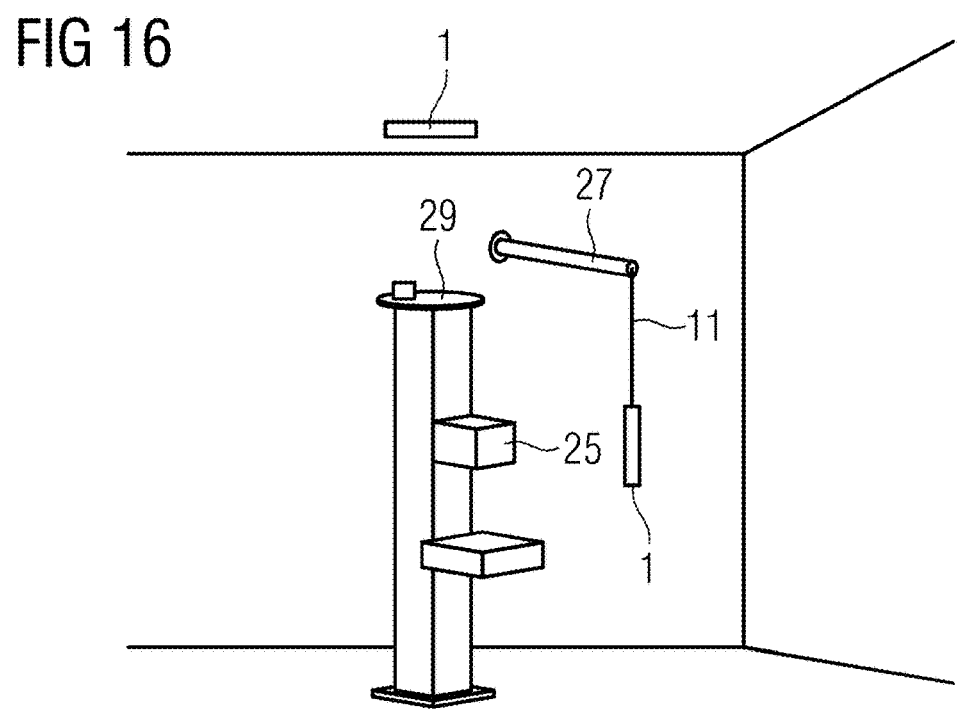
FIG. 16 shows a medical device, and a UV source of which the height is able to be adjusted by means of a cable, wherein the cable is once again fastened to a swivel arm, in accordance with one or more embodiments of the disclosure.
Figure 17:
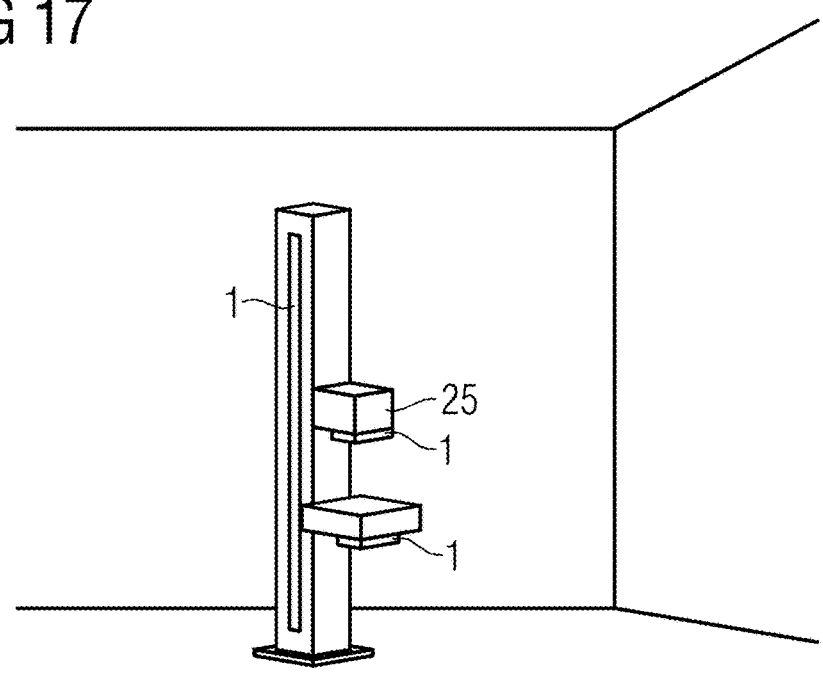
FIG. 17 shows a medical device with height-adjustable components on which UV sources are arranged, in accordance with one or more embodiments of the disclosure.

FIG. 16 shows a medical device 25, which may be irradiated by means of a UV source 1 attached height-adjustably to a cable 11. The medical device may, for example, involve a mammography system. The swivel arm 27 gives the UV source 1 an additional degree of freedom. In addition, there is a further UV source 1 located on the ceiling, which is used for irradiation from above. With this arrangement, the medical device may be irradiated from all around. Optionally, a parking and charging station 29 for a drone 30 may be positioned on a stand of the medical device. The drone may e.g. likewise be configured to disinfect surfaces by means of UV radiation surfaces. In accordance with one alternative form of embodiment, shown in FIG. 17, UV sources 1 may be arranged on the medical device 25 itself, e.g. on movable components of the medical device 25. It is also conceivable for the forms of embodiment of FIGS. 16 and 17 to be combined.

Figure 18:
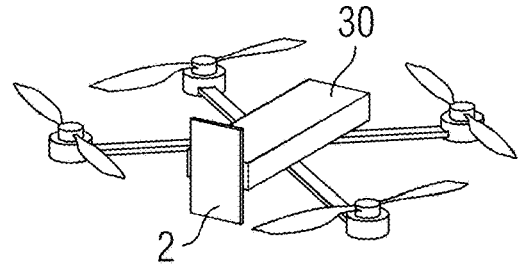
FIG. 18 shows a drone with a UV light-reflecting element, in accordance with one or more embodiments of the disclosure.
Figure 19:
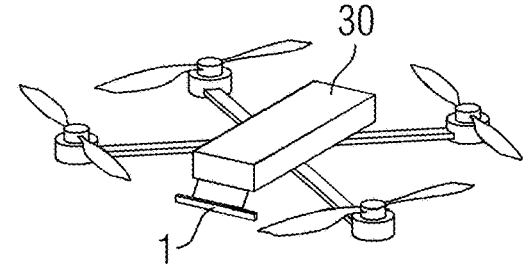
FIG. 19 shows a drone with a UV source, in accordance with one or more embodiments of the disclosure.

FIG. 18 shows a drone 30 with a UV light-reflecting element 2 ("passive drone" 30), e.g. a mirror. The drone may e.g. be employed flexibly to divert UV light into hard-to-access areas. In accordance with one alternative form of embodiment, a UV source 1 may be arranged on the drone 30 itself, as shown in FIG. 19 ("active drone" 30). The drone may thus take care of irradiation of e.g. hard-to-access areas or surfaces independently of external UV sources.

Figure 20:
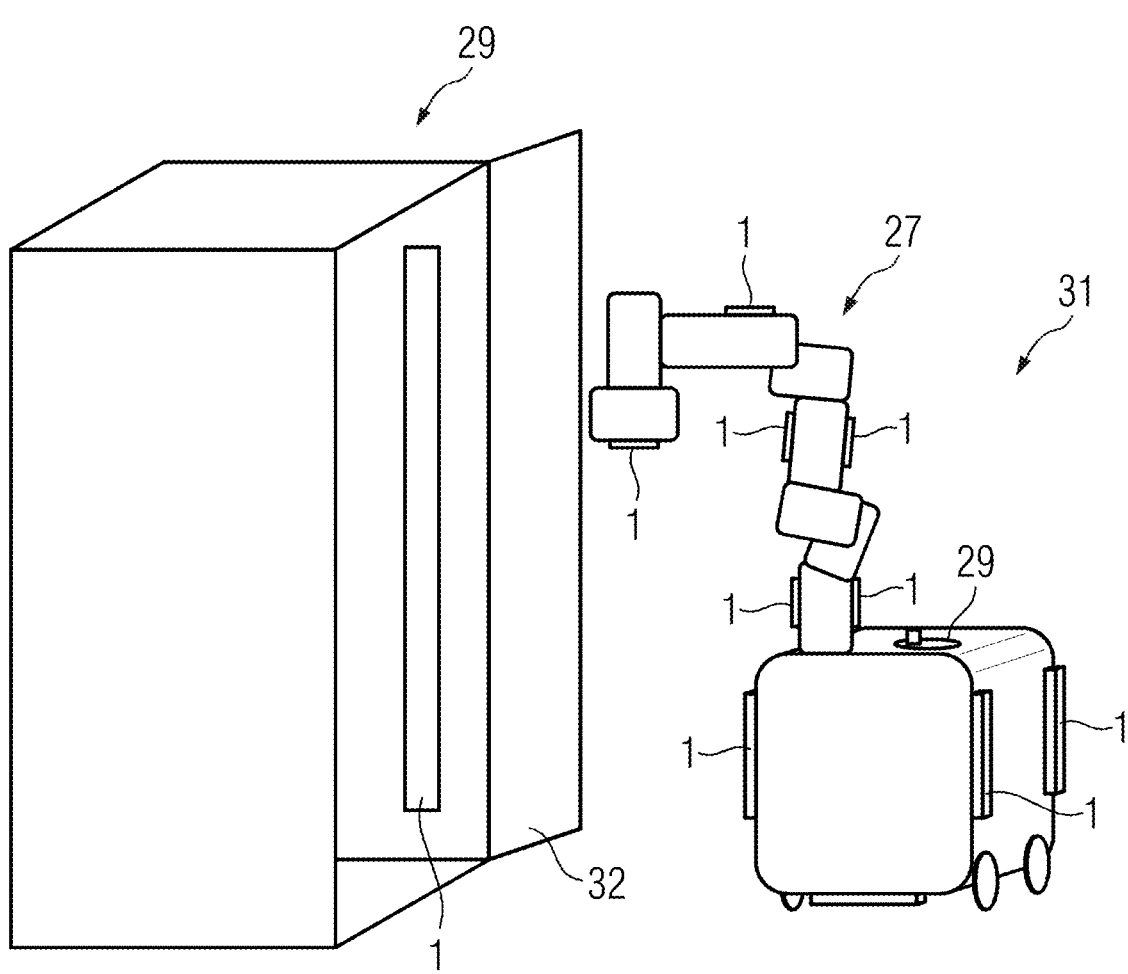
FIG. 20 shows a medical assistance robot, on which a plurality of UV sources are arranged as well as a parking and charging station for the assistance robot, in accordance with one or more embodiments of the disclosure.

FIG. 20 shows a medical assistance robot 31, on which a plurality of UV sources 1 is arranged. A number of UV sources 1 are arranged e.g. on a swivel arm 27 of the assistance robot 31, which may be flexibly aligned or brought into position by the swivel arm 27. The assistance robot 31 may be accommodated in a parking and charging station 29 and charged if necessary. The parking and charging station 29 in this form of embodiment UV comprises UV sources 1, which may be used for disinfection of the assistance robot 31 itself and where necessary of components that are carried by the assistance robot 31. The parking and charging station 29 may be closed by means of a door 32, e.g. closed UV-tight. Optionally, the assistance robot 31 may also have a parking and charging station 29 for a drone 30. Furthermore the assistance robot 31 may have sensors, e.g. cameras, and use these for orientation and/or for quality control.

Figure 21:
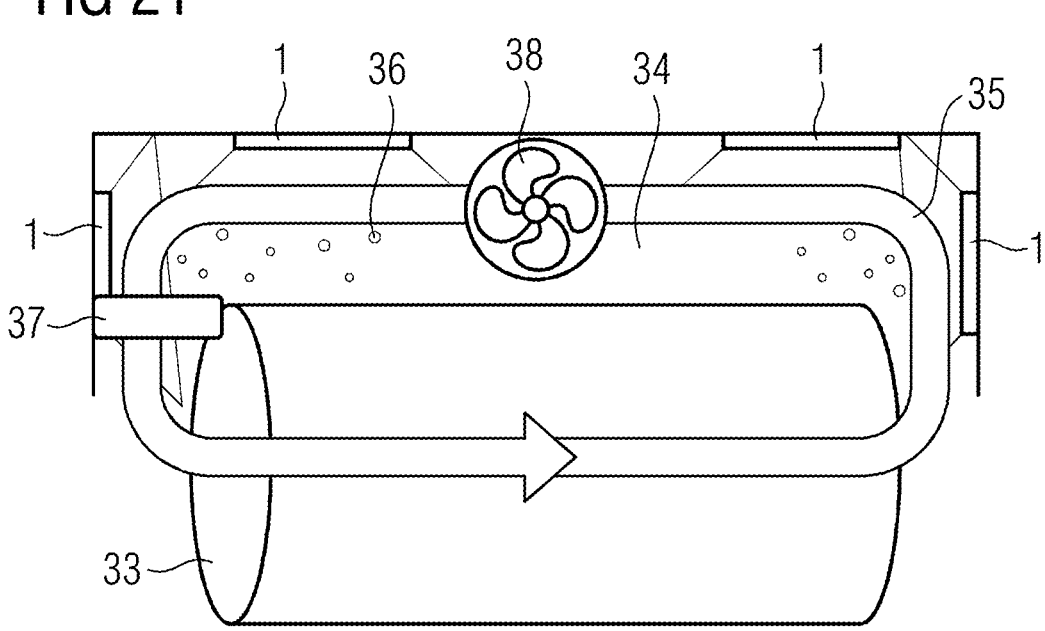
FIG. 21 shows a form of embodiment of a ventilation system for an examination area with integrated UV disinfection, in accordance with one or more embodiments of the disclosure.
Figure 22:
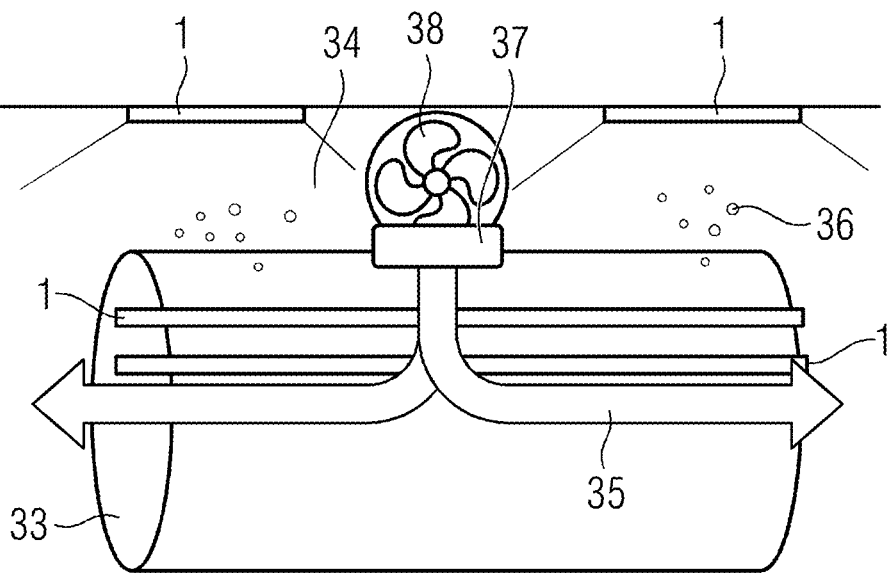
FIG. 22 shows a further form of embodiment of a ventilation system for an examination area with integrated UV disinfection, in accordance with one or more embodiments of the disclosure.

FIGS. 21 and 22 show a ventilation system for an examination area 33, of an MRT device for example, with integrated UV disinfection. A means for creating air flows 38 makes sure in this case that air 35 flowing through it may circulate. UV sources 1 are arranged in an air channel 3, which are designed to remove bacteria, viruses, and/or germs 36 by means of UV light. Optionally, a HEPA filter 37 may be arranged at the entrance to the air channel 34 to the examination area, which may take care of an additional filtering of the air 35 flowing through it. In the form of embodiment, which is shown in FIG. 21, the air is directed into the examination area 33 from the side. The form of embodiment, which is shown in FIG. 22, provides for a central air supply on the other hand. Furthermore, in FIG. 22 an optional additional UV source is shown inside the examination area 33, which may serve for example to disinfect the examination area 33 itself during pauses in examinations.

Figure 23:
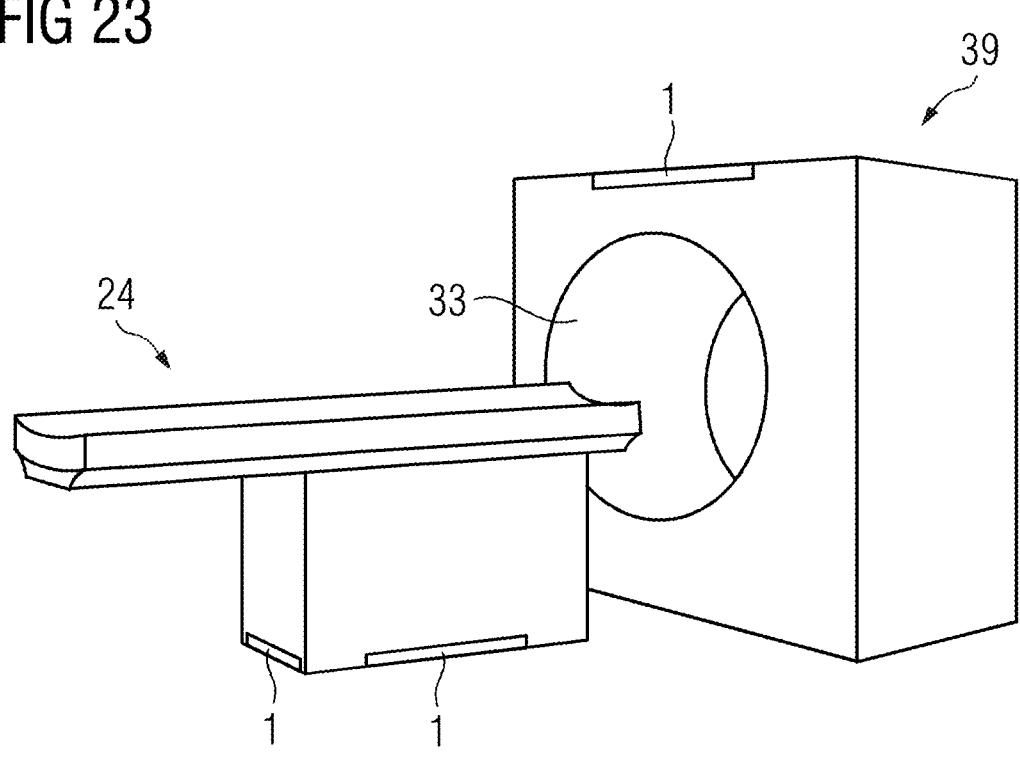
FIG. 23 shows a form of embodiment of a CT system with an examination area and a patient couch able to be moved into and out of the examination area and also with UV sources for disinfection of the patient couch, in accordance with one or more embodiments of the disclosure.
Figure 24:
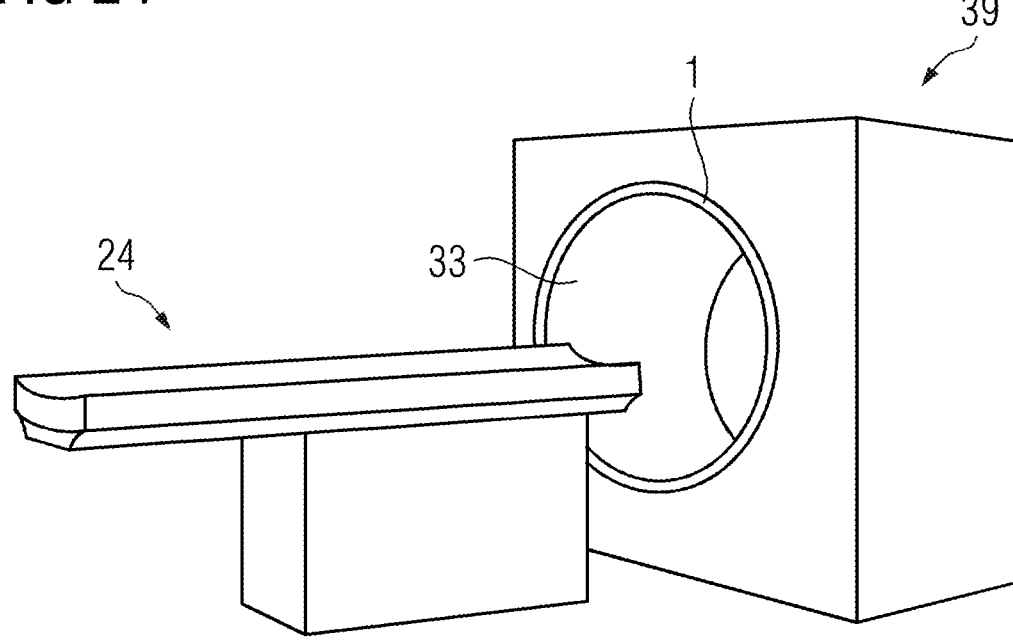
FIG. 24 shows an alternative form of embodiment of a CT system with an examination area and a patient couch able to be moved into and out of the examination area and also with UV sources for disinfection of the patient couch, in accordance with one or more embodiments of the disclosure.

FIGS. 23 and 24 show an MRT device or CT system 39 with an examination area 33 and a patient couch 24 that may be moved in and out. The patient couch in accordance with the form of embodiment in FIG. 23 may be disinfected by means of UV sources 1 fastened to the couch itself and to the upper end of the CT system. An annular arrangement of UV sources 1 at the entrance to the examination area 33 makes sure in the form of embodiment of FIG. 24 of a disinfection of the patient couch 24. In this case, the mobility of the patient couch 24 is utilized e.g. to make possible a complete disinfection. Basically the forms of embodiment of FIGS. 23 and 24 may also be combined to make possible a more thorough disinfection.

Figure 25:
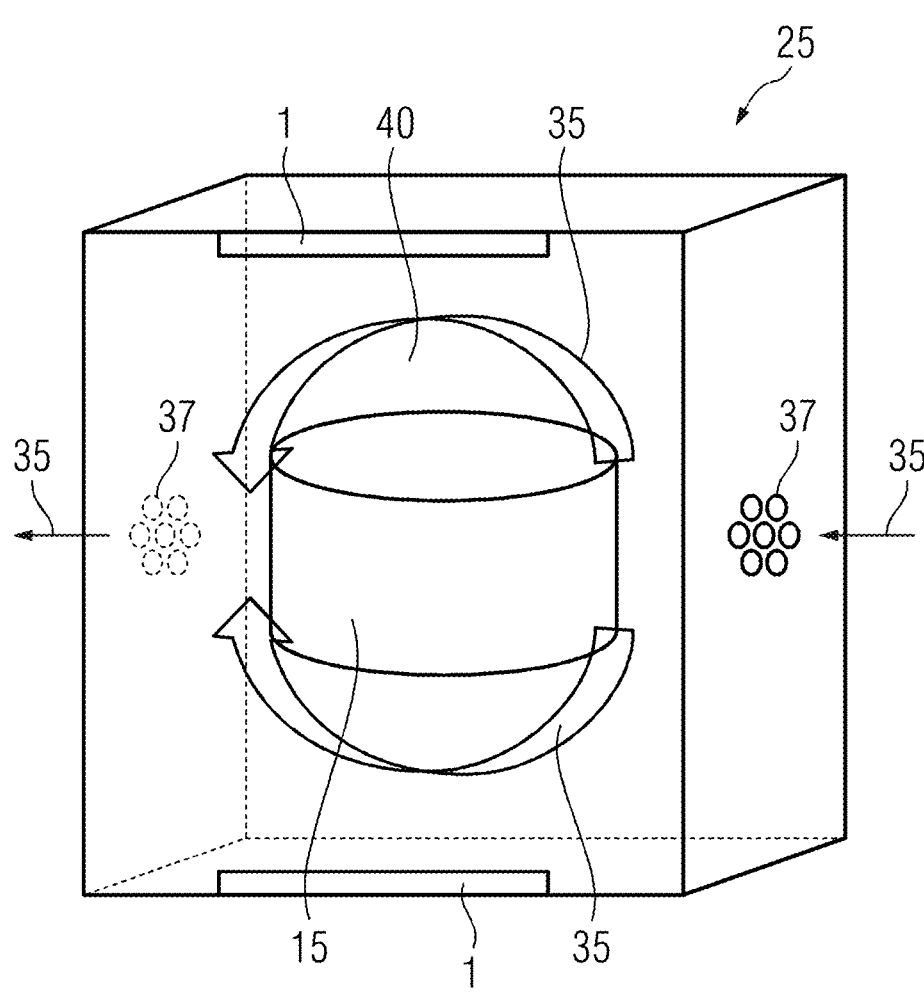
FIG. 25 shows a medical device with a ventilation system and an area able to be irradiated with UV radiation, through which a flow of air is directed, in accordance with one or more embodiments of the disclosure.

FIG. 25 shows a medical device 25 with a ventilation system and an area 40 able to be irradiated with UV radiation, wherein the UV radiation is emitted by two UV sources 1 arranged in the device. The ventilation serves e.g. to cool a component 15 of the medical device, but may also be used however or disinfection of the air 35 flowing through the area 40 able to be irradiated with UV radiation. Use is made here of the fact that, for ventilation of the component 15, air is sucked into the device 25 in any event, which may now be disinfected by UV light as it flows through. Optionally, HEPA filters 37 may be attached to the ventilation entry and/or exit, in order to bring about additional air cleaning by filtration.

Figure 26:
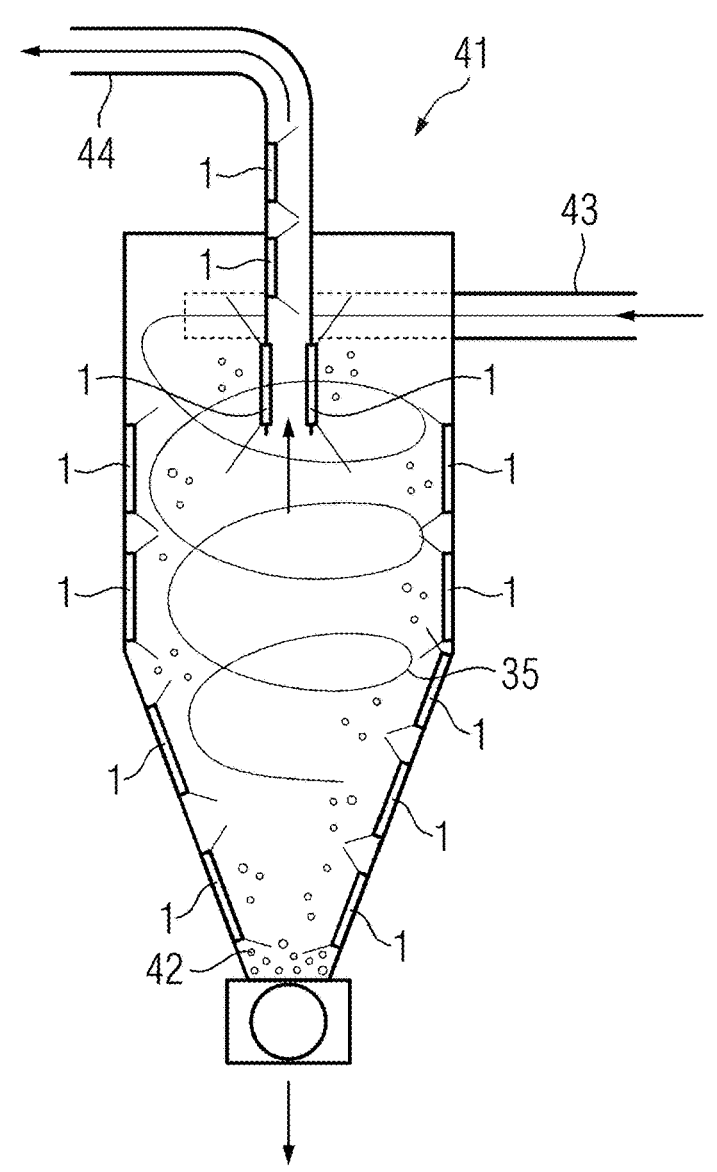
FIG. 26 shows a cyclone filter with UV sources arranged inside, in accordance with one or more embodiments of the disclosure.

FIG. 26 shows a cyclone filter 41 which, by air circulation within it, may bring about a separation of particles 42 from the air. In this case, the air 35 flows through the entrance 43, then circulates downwards in a spiral, wherein particles 42 are separated out at the bottom, and then leaves the cyclone filter 41 again in the middle at the top 42. By arranging UV sources on the inner walls of the cyclone filter 41, the air may in this case additionally be freed from viruses, bacteria and/or germs.

Figure 27:
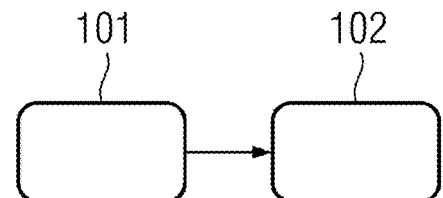
FIG. 27 shows a schematic diagram of a method for disinfection, in accordance with one or more embodiments of the disclosure.

FIG. 27 shows a schematic of a method for disinfection by means of UV light in accordance with the present disclosure. In this figure, in a first step 101, a disinfection mode is activated in order to irradiate surfaces and thus to disinfect them. This may be triggered for example by a user entry or a predetermined event, e.g., by a sensor detecting that there is no longer anybody located at the medical device, in the examination area or in the examination room. In a second step 102, the UV source is moved by means of components able to be moved mechanically for the purpose of medical examination and/or treatment into a specific position or on a specific path, wherein the UV source illuminates and thus disinfects surfaces. The movement in this case may e.g. take place automatically based on a predetermined movement pattern and/or based on sensor data detected by a sensor unit 13.

Although the disclosure has been illustrated and described in greater detail by the exemplary embodiments given, the disclosure is not restricted by the disclosed examples and other variations may be derived herefrom by the person skilled in the art, without departing from the scope of protection of the disclosure.

What is claimed is:

1. A system for disinfection of surfaces, comprising:
a medical component associated with one or more of (i) a medical device, (ii) an item of equipment of a medical examination, or (iii) a treatment room for a medical examination; and
an ultraviolet (UV) light source coupled to and integrated as part of the medical component, the UV light source being configured to perform disinfection irradiation of at least one surface to perform a medical examination and/or treatment;
a controller configured to selectively operate the system in an examination mode and a disinfection mode,
wherein the medical component is configured to be moved mechanically in (i) the examination mode for the purpose of the medical examination and/or the treatment, and (ii) the disinfection mode distinct from the examination mode for the purpose of performing a disinfection cycle, wherein the controller is configured, in response to a triggering condition being satisfied, to switch the system from operating in the examination mode to operating in the disinfection mode and perform the disinfection cycle, and wherein the UV light source is configured, during the disinfection mode, to generate UV light and to be moved via movement of the medical component in accordance with a predetermined movement pattern, which differs from movement of the medical component during the examination mode, to thereby perform the disinfection irradiation.

2. The system as claimed in claim 1, wherein the medical component comprises a movably-arranged x-ray source, and wherein the UV light source is arranged on the movably-arranged x-ray source.

3. The system as claimed in claim 1, wherein the medical component comprises a movably arranged x-ray detector, and wherein the UV light source is arranged on the movably arranged x-ray detector.

4. The system as claimed in claim 1, wherein the medical component comprises an x-ray device or a C-arm system, and wherein the UV light source is arranged on a cladding of the x-ray device or the C-arm system.

5. The system as claimed in claim 1, wherein the UV light source is arranged on one of a wall mount, a floor mount, a ceiling mount, a swivel arm, or a cable.

6. The system as claimed in claim 1, wherein the UV light source is configured to be placed at, on, or above an operating device.

7. The system as claimed in claim 6, wherein the operating device comprises a UV-transparent component.

8. The system as claimed in one claim 1, wherein the UV light source is arranged on the medical component such that at least a portion of a further medical device is irradiated when the medical component is laid on or passed through the medical device.

9. The system as claimed in claim 8, wherein the medical component comprises a sensor configured to detect a presence of the further medical device and/or contaminations.

10. The system as claimed in claim 1, further comprising:
a UV light-reflecting element configured to reflect and direct the UV light generated via the UV light source to other areas in addition to areas directly exposed to the generated UV light.

11. The system as claimed in claim 1, further comprising:
a sensor configured to detect one of (i) a radiation dose, (ii) a presence of humans and/or devices, (iii) a position of humans and/or devices, and (iv) a macroscopic surface contamination.

12. The system as claimed in claim 1, wherein the UV light source is from among a plurality of UV light sources, the UV light source being arranged in and/or on an examination area of a medical imaging device, and further comprising:
a means for creating an air flow configured to move air into an area to be irradiated with the UV light via the plurality of UV light sources; and
an examination area ventilation system comprising an air channel identified with the air flow in which the plurality of UV light sources are arranged to irradiate air flowing through the air channel.

13. The system as claimed in claim 1, wherein the triggering condition comprises a determination, via a sensor, that a person is no longer in a region in which the disinfection irradiation is to be performed.

14. The system as claimed in claim 1, wherein the UV light source is configured, during movement in accordance with the predetermined movement pattern, to vary a UV radiation intensity of the disinfection irradiation.

15. The system as claimed in claim 14, wherein the UV light source is configured to vary the UV radiation intensity of the disinfection irradiation based upon a type of medical examination previously performed via the medical component.

16. A method for disinfection of surfaces with an ultraviolet (UV) light source that is coupled to and integrated as part of a medical component, the method comprising:
selectively controlling, via a controller, the medical component to be moved mechanically in (i) an examination mode for the purpose of a medical examination and/or a treatment, and (ii) a disinfection mode distinct from the examination mode for the purpose of performing a disinfection cycle;
in response to a triggering condition being satisfied, switching, via the controller, from the examination mode to the disinfection mode; and
performing, during the disinfection mode, the disinfection cycle by moving the UV light source via movement of the medical component in accordance with a predetermined movement pattern, which differs from movement of the medical component during the examination mode, to thereby perform the disinfection irradiation.

* * * * *